United States Patent [19]

Onodera et al.

[11] Patent Number: 5,221,593
[45] Date of Patent: Jun. 22, 1993

[54] SILVER HALIDE PHOTOGRAPHIC MATERIALS CONTAINING NOVEL NUCLEATING AGENT

[75] Inventors: Akira Onodera; Yasushi Usagawa, both of Hino, Japan

[73] Assignee: Konica Corporation, Tokyo, Japan

[21] Appl. No.: 665,686

[22] Filed: Mar. 7, 1991

[30] Foreign Application Priority Data

Mar. 9, 1990 [JP] Japan .................................... 2-59026

[51] Int. Cl.$^5$ ........................... G03C 1/06; G03C 1/34
[52] U.S. Cl. ..................................... 430/264; 430/598; 430/940
[58] Field of Search ......................... 430/264, 598, 940

[56] References Cited

U.S. PATENT DOCUMENTS

| 4,971,888 | 11/1990 | Okada et al. | 430/264 |
| 4,988,604 | 1/1991 | Machonkin et al. | 430/264 |
| 5,028,510 | 7/1991 | Okamura et al. | 430/264 |

FOREIGN PATENT DOCUMENTS

| 0311009 | 4/1989 | European Pat. Off. |
| 0345025 | 12/1989 | European Pat. Off. |
| 60-170843 | 9/1985 | Japan |
| 2107074 | 4/1983 | United Kingdom |

OTHER PUBLICATIONS

Patents Abstracts of Japan vol. 10, No. 15 (P–422) (2072), 21 Jan. 1986; & JP-A-60170843 (Konishiroku) Apr. 9, 1985.

*Primary Examiner*—Charles L. Bowers, Jr.
*Assistant Examiner*—Janet C. Baxter
*Attorney, Agent, or Firm*—Frishauf, Holtz, Goodman & Woodward

[57] ABSTRACT

The improved silver halide photographic material contains a novel nucleating compound that is useful either as a contrast increasing agent in light-sensitive material for use in photochemical processes or as a foggant in direct positive light-sensitive materials.

7 Claims, No Drawings

SILVER HALIDE PHOTOGRAPHIC MATERIALS CONTAINING NOVEL NUCLEATING AGENT

BACKGROUND OF THE INVENTION

This invention relates to a silver halide photographic material, more particularly to a photographic material that contains a compound capable of working as a novel nucleating agent.

Nucleating agents are known to be used as contrast increasing agents in silver halide photographic materials in photochemical processes. They are also known be useful as foggants in direct positive-acting silver halide photographic materials.

The photochemical process includes the step of converting the change of density in a continuous tone image to a set of halftone dots having areas proportional to the image density, and silver halide photographic materials having contrasty photographic characteristics are generally used in this step. In order to impart contrasty characteristics to image, hydrazine compounds are contained as "contrast increasing agents" in silver halide photographic materials and, in addition, silver halide grains that help these compounds exhibit the inherent contrasty characteristics effectively are used or other appropriate photographic additives are used in combination with those hydrazine compounds in such a way as to obtain desired photographic materials. For details of these techniques, see JP-A-56-106244 (the term "JP-A-" as used herein means an "unexamined published Japanese patent application"), U.S. Pat. No. 4,686,167 and European Pat. No. 333,435. The silver halide photographic materials are indeed stable light-sensitive materials and can produce high-contrast photographic image even if they are processed with developing solutions adapted for rapid processing.

However, if these photographic materials are used in the step of converting a continuous tone image to a halftone image, sandlike fog or pepper fog which are generally referred to as "black dots" can occur in halftone dots, leading to impaired dot quality. In an attempt at solving this problem, various stabilizers or restrainers having hetero atoms have been added but this has not always proved to be a complete solution. Under these circumstances, a light-sensitive material that uses an effective contrast increasing agent free from that problem is desired.

A known method of forming a positive image using a direct positive-acting silver halide photographic material is to perform imagewise exposure using a yet to be fogged internal latent image forming silver halide emulsion and to conduct surface development in the presence of a foggant, thereby producing a positive image. Various techniques of this approach have been known and are described in such prior patents as U.S. Pat. Nos. 2,592,250, 2,456,957, 2,497,875, 2,588,982, British Patent No. 1,151,363, JP-B-43-29405 (the term "JP-B" as used herein means an "examined Japanese patent publication"), JP-A-47-9434, 47-9677, 47-32813, 47-32814, 48-9727, 48-9717, U.S. Pat. Nos. 3,761,266, 3,496,577, and JP-A-50-8524 and 50-38525.

Hydrazine compounds are known as useful foggants. Exemplary hydrazine compounds that have been used as foggants include the hydrazine compounds described in U.S. Pat. Nos. 2,563,785 and 2,588,982, the naphthylhydrazinesulfinic acid described in U.S. Pat. No. 2,064,700, and the sulfomethylhydrazines described in British Patent No. 1,403,018. JP-B-41-17184 teaches that a positive color image can be produced using hydrazide or hydrazone compounds. However, the use of these hydrazine compounds has the problem that the induction period (the time required for image to become visible upon development) is longer than in the case of ordinary development with latent-image silver and, hence, the development with these compounds is considerably retarded.

Another problem with the prior art is that when it is applied to multi-layered color photographic materials, unevenness is likely to occur in photographic characteristics between layers or the finally obtained maximum density is low.

Further, development is conventionally performed at pHs higher then 12 in order to maintain desired fogging action, thereby assuring satisfactory results. However, this approach is by no means advisable since it either causes significantly accelerated deterioration of developing agents or impairs the film properties of the processed photographic material. Therefore, it is also desired to develop direct positive silver halide photographic material that uses an advantageous foggant free from the aforementioned problems.

SUMMARY OF THE INVENTION

An object, therefore, of the present invention is to provide a silver halide photographic material that not only has contrasty photographic characteristics but also is capable of exhibiting high-contrast photographic characteristics by restraining the fog that would otherwise occur in a halftone image.

Another object of the present invention is to provide a light-sensitive material which, when used as a direct positive silver halide photographic material, is capable of attaining a satisfactorily high maximum density (Dmax) by development with a low-pH developing solution, that provides a satisfactory image of high maximum density and low minimum density by short fogging development, and that will experience only a small increase in minimum density even if it is stored for a while before exposure.

These objects of the present invention can be attained by a silver halide photographic material that has at least one silver halide emulsion layer and that is characterized by containing at least one compound represented by the following general formula (I) (which is hereinafter sometimes referred to as the "compound of the present invention"):

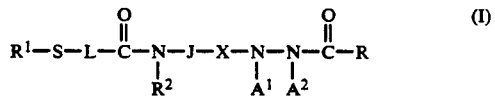

where $R^1$ is an alkyl group, an alkenyl group, an alkynyl group, an aryl group or a hetero cyclic ring; $R^2$ is a hydrogen atom, an alkyl group, an aryl group or a hetero cyclic ring; R is a hydrogen atom or a blocking group; L is an alkylene or alkenylene group; J is a linkage group; X is an aromatic or heterocyclic residue; $A^1$ and $A^2$ are each a hydrogen atom, or either one of them is a hydrogen atom and the other is an acyl, sulfonyl or oxalyl group.

DETAILED DESCRIPTION OF THE INVENTION

In the general formula (I), $R^1$ represents an alkyl group (e.g. methyl, ethyl, i-propyl, butyl, t-butyl, hexyl, octyl, t-octyl, decyl, dodecyl, tetradecyl, cyclohexyl, cyclohexylmethyl, benzyl, etc.) an alkyl group substituted by at least one group selected from among aryl, hetero cyclic ring, hydroxy, unsubstituted alkoxy, sulfonamido, aryloxy, ureido, carbamoyl, acylamino and sulfamoyl. $R_1$ also represents an alkenyl group (e.g. allyl, 1-propenyl, 1,3-butadienyl, 2-butenyl, 2-pentenyl, cinnamyl, etc.), an alkynyl group (e.g. propargyl, 2-butynyl, etc.), an aryl group (e.g. phenyl, tolyl, di-i-propylphenyl, naphthyl, etc.), and a hetero cyclic ring (e.g. pyridyl, furyl, tetrahydrofuryl, thienyl, oxazolyl, benzoxazolyl, benzothiazolyl, etc.). These groups may have substituents such as alkyl, aryl, hetero cyclic ring, alkoxy, aryloxy, hydroxy, halogen, amino, alkylamino, arylamino, acylamino, sulfonamido, ureido, etc.

In the general formula (I), $R^2$ represents a hydrogen atom, an alkyl group (e.g. methyl, ethyl, methoxyethyl, benzyl, etc.), an aryl group (e.g. phenyl, naphthyl, methoxyphenyl, etc.) or a hetero cyclic ring (e.g. pyridyl, thienyl, furyl, tetrahydrofuryl, etc.).

In the general formula (I), R represents a hydrogen atom or a blocking group and preferred examples of the blocking group include: an alkyl group (e.g. methyl, ethyl, benzyl, methoxymethyl, trifluoromethyl, phenoxymethyl, hydroxymethyl, methylthiomethyl, phenylthiomethyl, etc.), an aryl group (e.g. phenyl, chlorophenyl, 2-hydroxymethylphenyl, etc.), a hetero cyclic ring (e.g. pyridyl, thienyl, furyl, etc.),

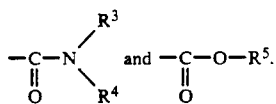

In the last two groups, $R^3$ and $R^4$ each represents a hydrogen atom, an alkyl group (e.g. methyl, ethyl, benzyl, etc.), an alkenyl group (e.g. allyl, butenyl, etc.), an ankynyl group (e.g. propargyl, butynyl, etc.), an aryl group (e.g., phenyl, naphthyl, etc.), a hetero cyclic ring (e.g. 2,2,6,6-tetramethylpiperidinyl, N-ethyl-N'-ethyl-pyrazolidinyl, pyridyl, etc.), a hydroxyl group, an alkoxy group (e.g. methoxy, ethoxy, etc.) and an amino group (e.g. amino, methylamino, etc.), provided that $R^3$ and $R^4$ may combine with the nitrogen atom to form a ring (e.g. piperidino, morpholino, etc.). In said groups, $R^5$ represents a hydrogen atom, an alkyl group (e.g. methyl, ethyl, hydroxyethyl, etc.), an alkenyl group (e.g. allyl, butenyl, etc.), an alkynyl (e.g. propargyl, butynyl, etc.), an aryl group (e.g. phenyl, naphthyl, etc.), a hetero cyclic ring (e.g. 2,2,6,6-tetramethylpiperidinyl, N-methylpiperidinyl, pyridyl, etc.).

In the general formula (I). L represents an alkylene group (e.g. methylene, ethylene, trimethylene, methylmethylene, ethylmethylene, butylmethylene, hexylmethylene, decylmethylene, etc.), or an alkenylene group (e.g. propenylene, butenylene, etc.).

In the general formula (I), J represents a linkage group as specifically exemplified by an acylamino group (e.g. benzoylamino or phenoxyacetylamino), a sulfonamido group (e.g. benzenesulfonamido or furansulfonamido), a ureido group (e.g. ureido or phenylureido), an alkylamino group (e.g. benzylamino or furfurylamino), an anilino group, an alkylideneamino group (e.g. benzylideneamino), an aryloxy group (e.g. phenoxy), an aminocarbonylalkoxy group (e.g. aminocarbonylmethoxy), a sulfonylhydrazinocarbonylamino (e.g. benzenesulfonylhydrazinocarbonylamino).

In the general formula (I), X represents an aromatic residue (e.g. phenylene, naphthylene, etc. which may be optionally substituted) or a heterocyclic residue (e.g. pyridine, pyrazole, pyrrole, thiophene, benzothiophene, furan, etc. which may be optionally substituted).

In the general formula (I), $A^1$ and $A^2$ are each a hydrogen atom, or either one of them is a hydrogen atom and the other is an acyl group (e.g. acetyl or trifluoroacetyl), a sulfonyl group (e.g. methanesulfonyl or toluenesulfonyl) or an oxalyl group (e.g. ethoxalyl). Preferably, both $A^1$ and $A^2$ are a hydrogen atom.

Representative examples of the compound (I) are listed below specifically but it should of course be understood that the compounds (I) that can be used in the present invention are by no means limited to the following examples.

Exemplary compounds (I)

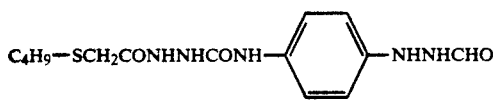

I-1

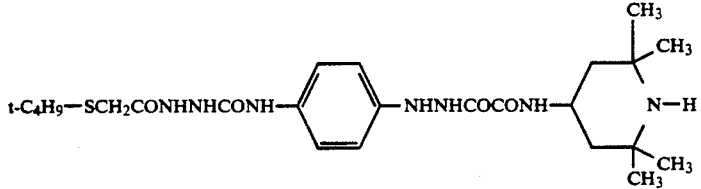

I-2

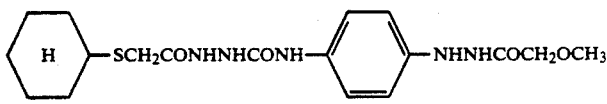

I-3

-continued
Exemplary compounds (I)
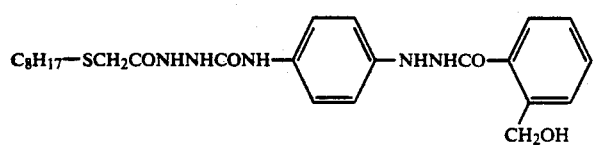
I-4
I-5
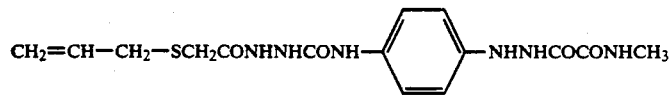
I-6
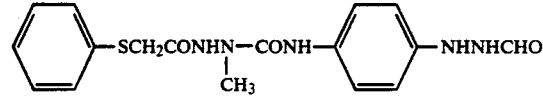
I-7
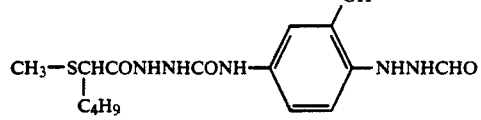
I-8
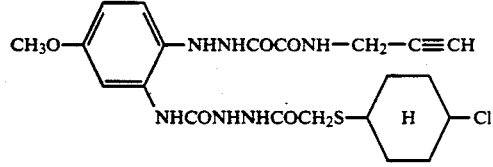
I-9
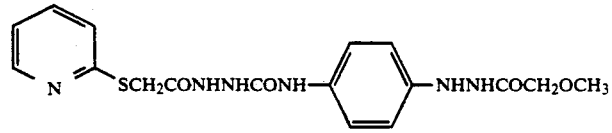
I-10
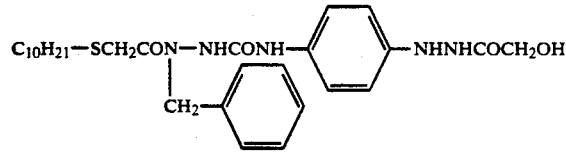
I-11
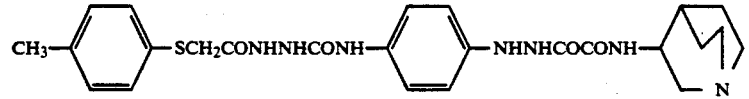
I-12
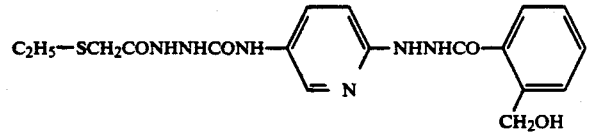
I-13
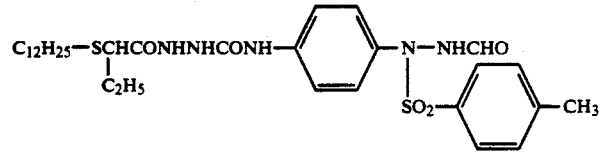
I-14

-continued
Exemplary compounds (I)
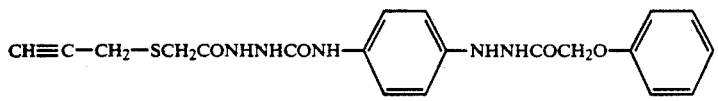
I-15
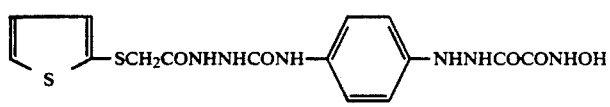
I-16
I-17
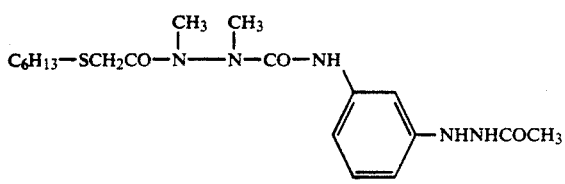
I-18
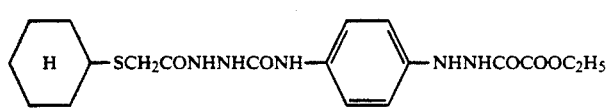
I-19
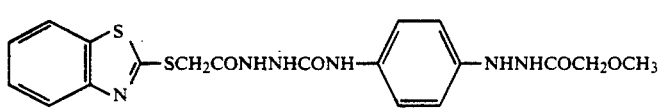
I-20
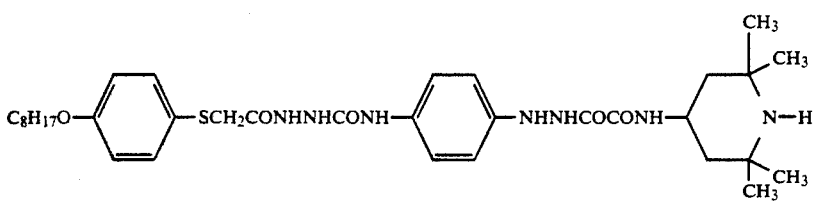
I-21
I-22
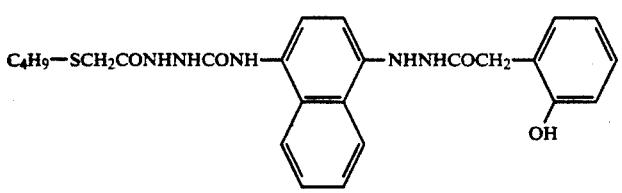
I-23
I-24
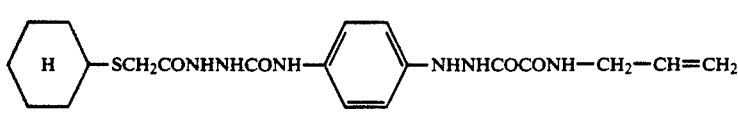
I-25

-continued
Exemplary compounds (I)
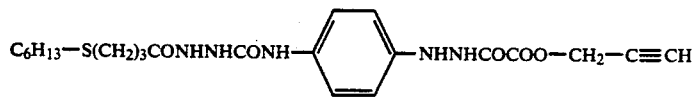
I-26
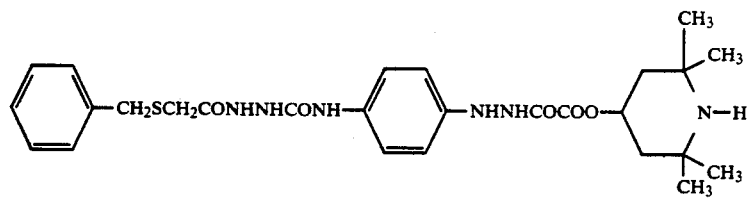
I-27
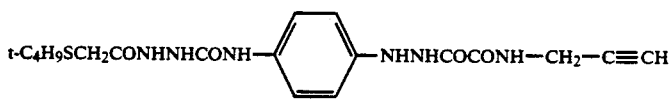
I-28
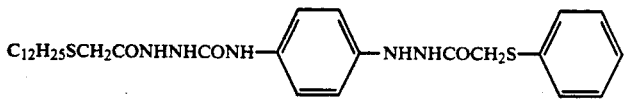
I-29
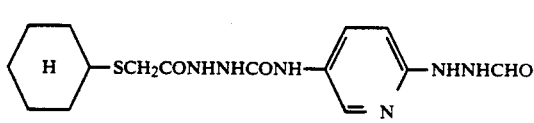
I-30
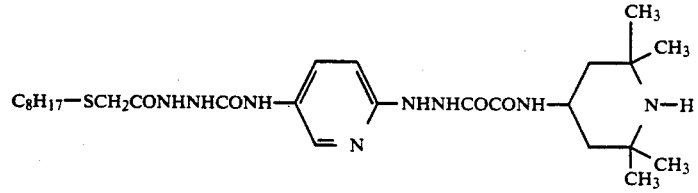
I-31
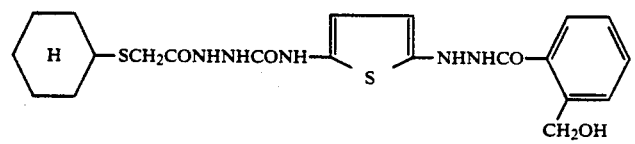
I-32
I-33
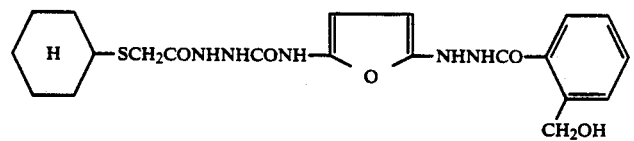
I-34
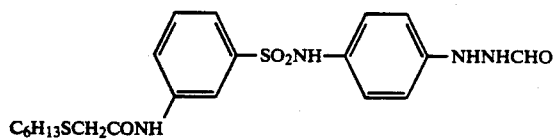
I-35
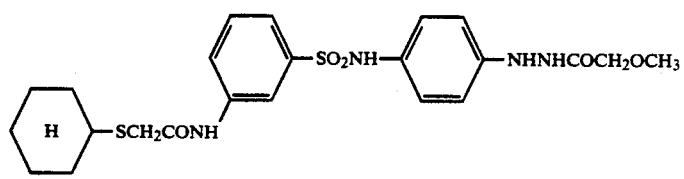
I-36

-continued
Exemplary compounds (I)
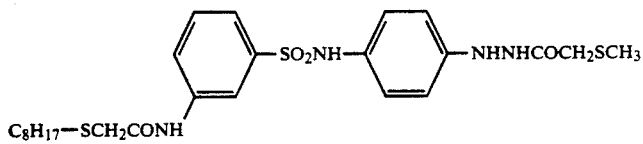
I-37
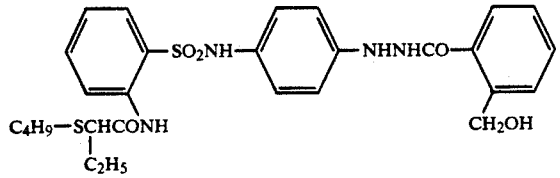
I-38
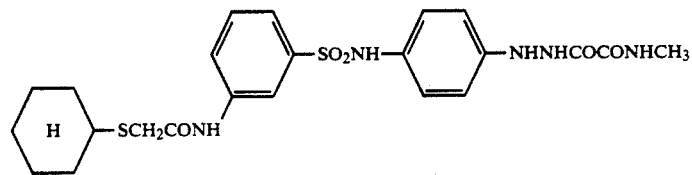
I-39
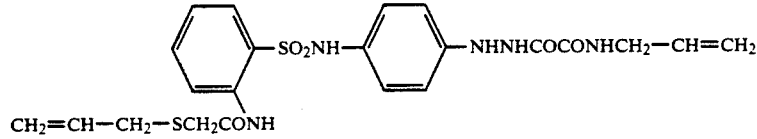
I-40
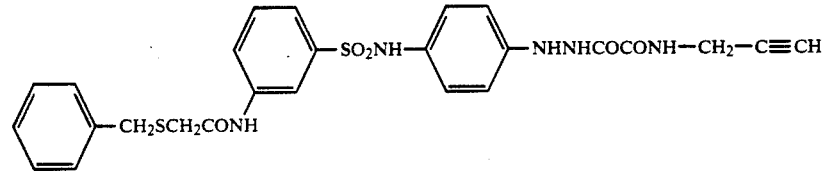
I-41
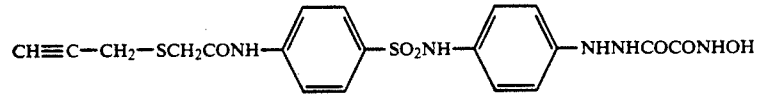
I-42
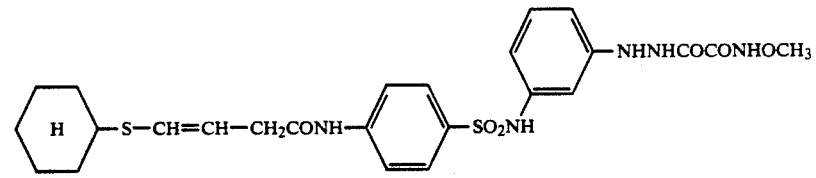
I-43
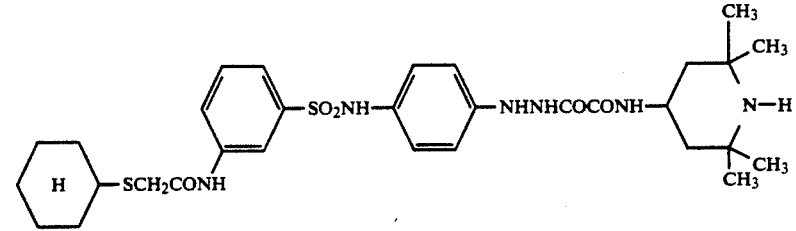
I-44
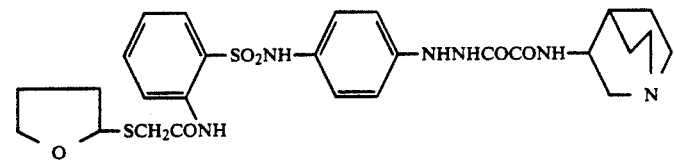
I-45

-continued
Exemplary compounds (I)
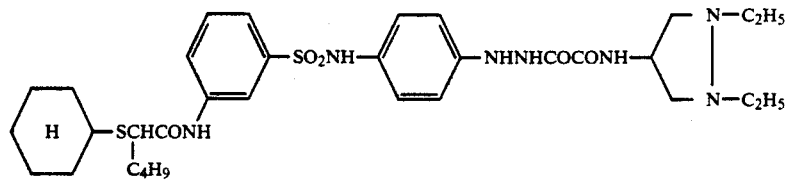 I-46
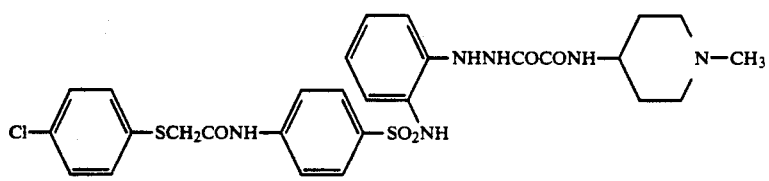 I-47
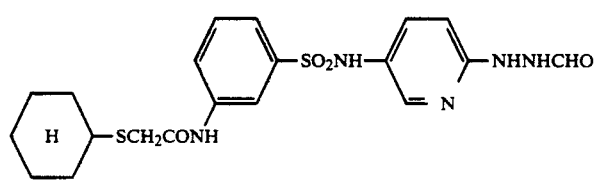 I-48
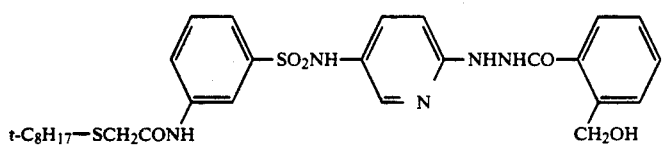 I-49
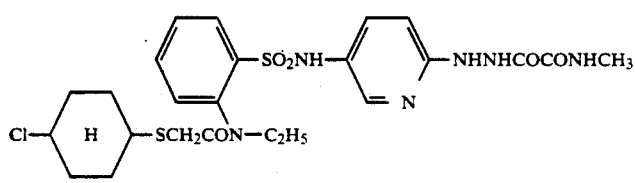 I-50
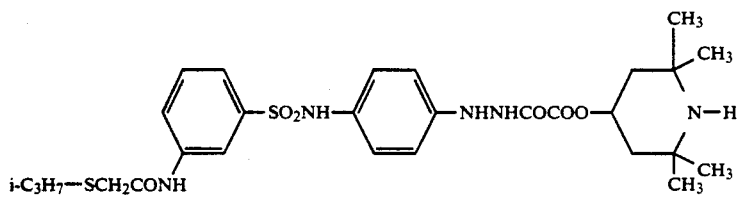 I-51
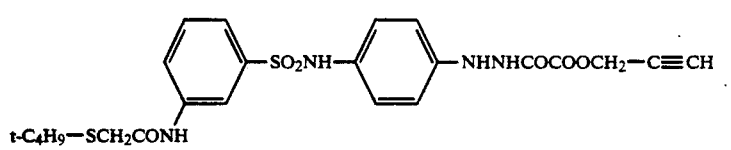 I-52
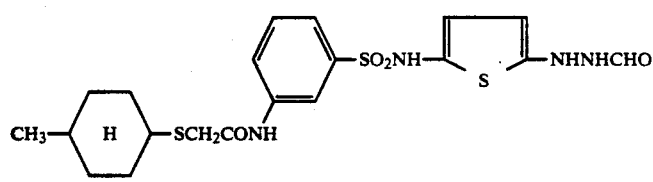 I-53
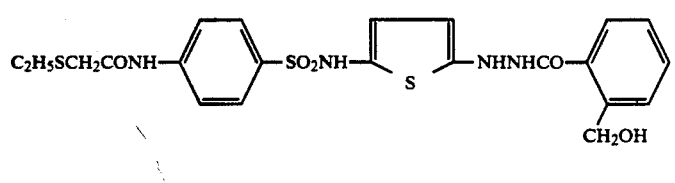 I-54

-continued
Exemplary compounds (I)
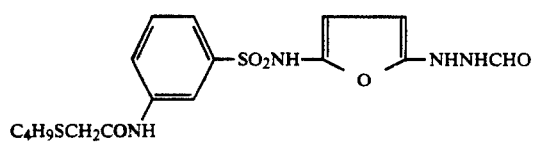
I-55
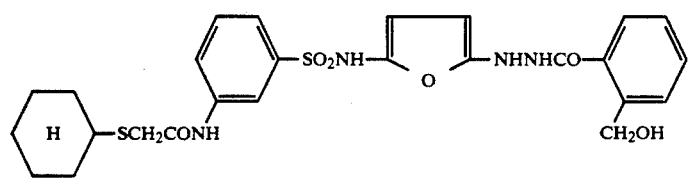
I-56
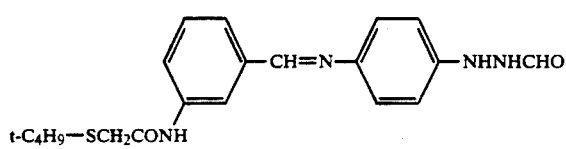
I-57
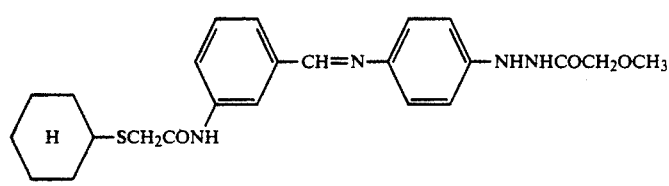
I-58
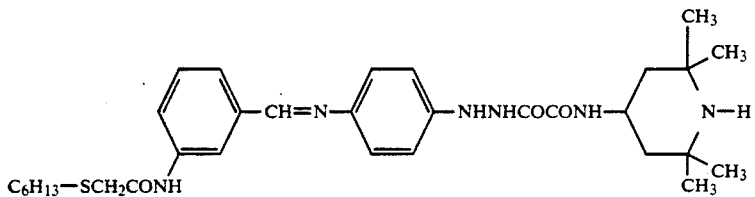
I-59
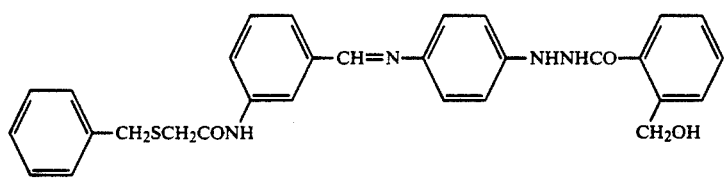
I-60
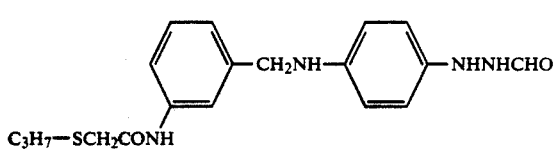
I-61
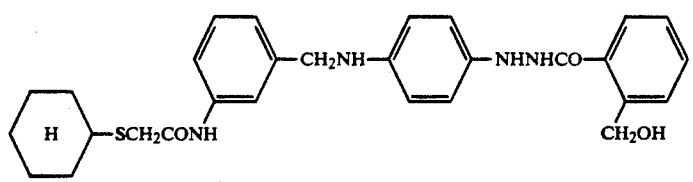
I-62
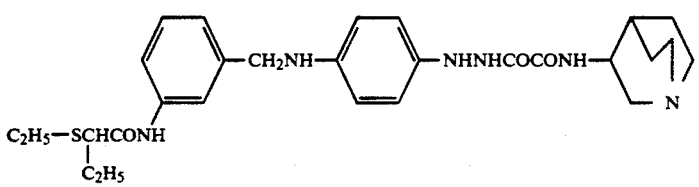
I-63

-continued
Exemplary compounds (I)
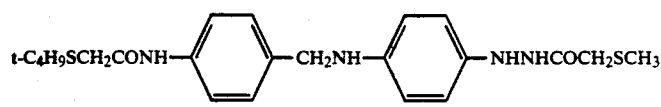
I-64
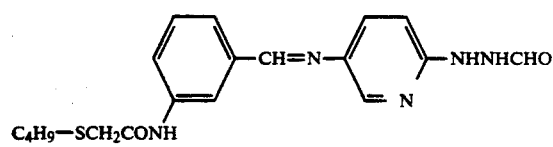
I-65
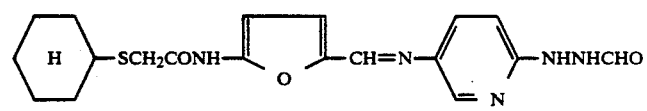
I-66
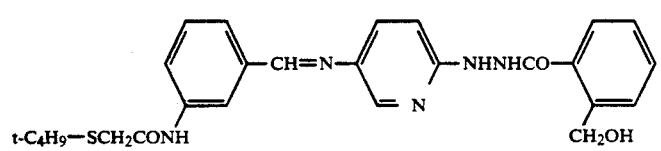
I-67
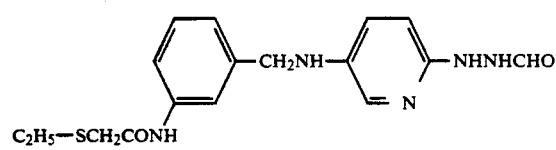
I-68
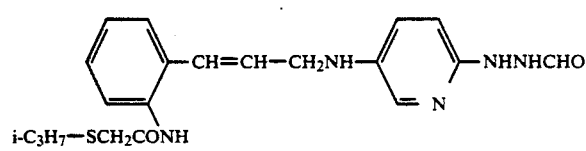
I-69
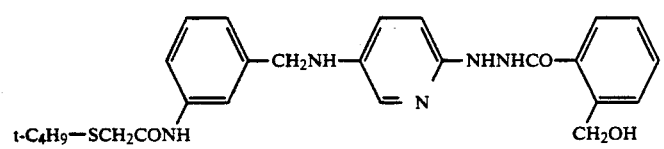
I-70
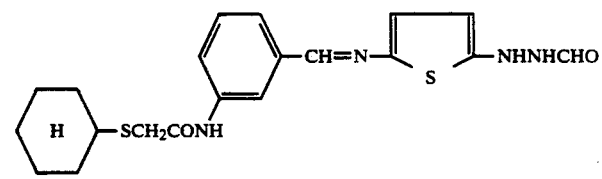
I-71
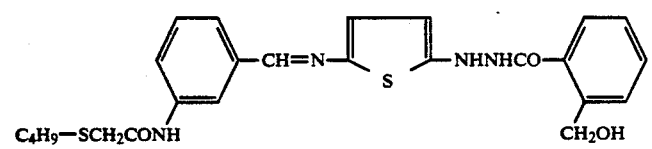
I-72
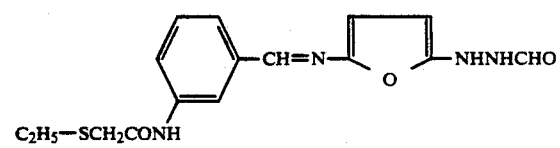
I-73

-continued
Exemplary compounds (I)
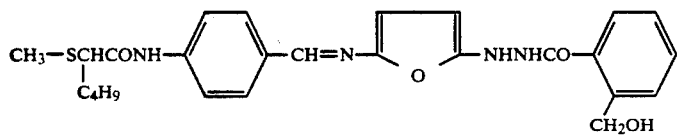  I-74
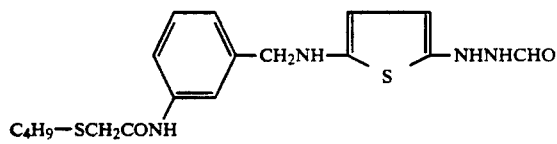  I-75
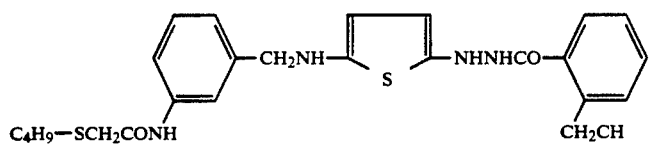  I-76
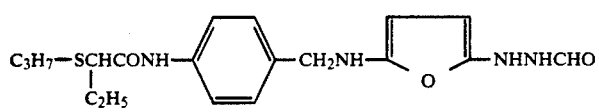  I-77
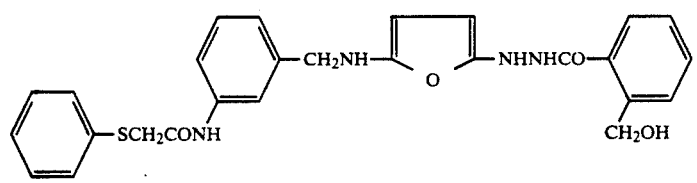  I-78
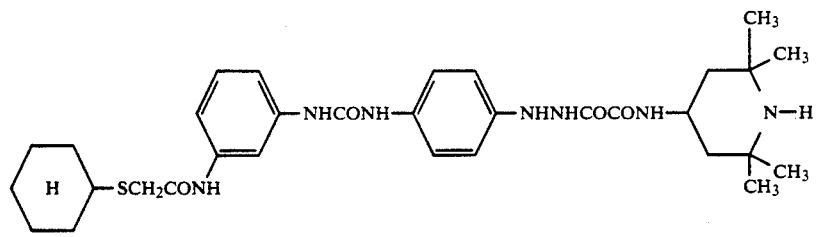  I-79
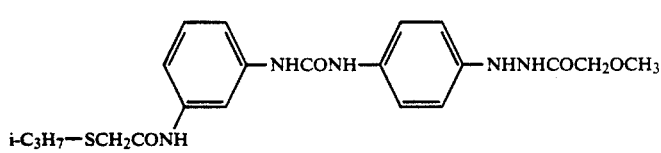  I-80
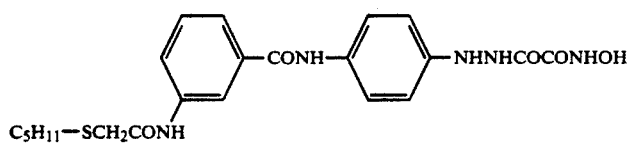  I-81
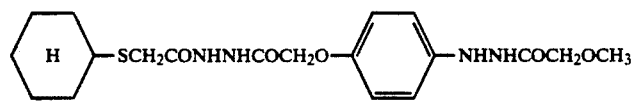  I-82
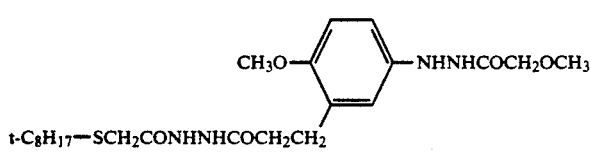  I-83

-continued
Exemplary compounds (I)
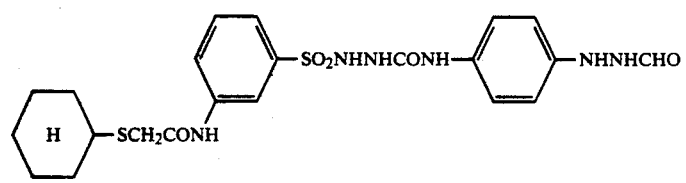
I-84
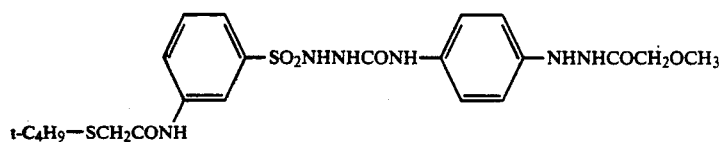
I-85
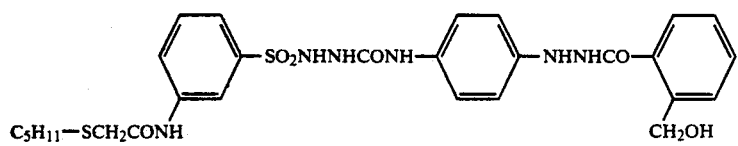
I-86
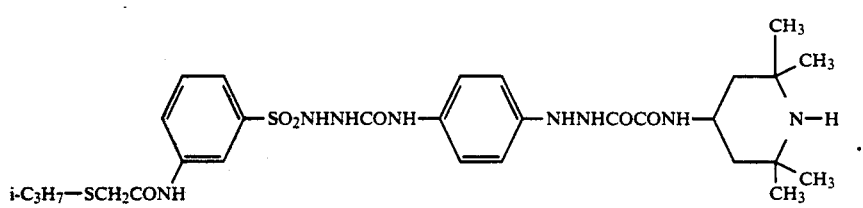
I-87
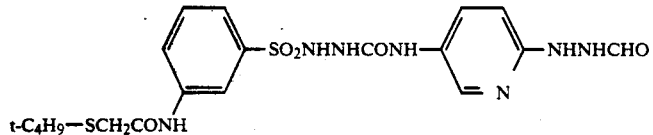
I-88
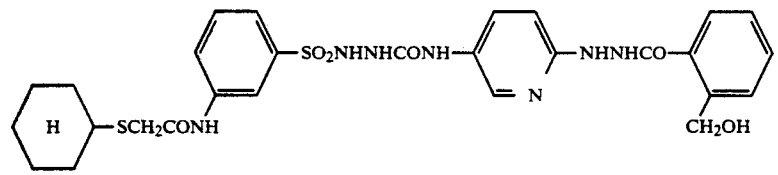
I-89
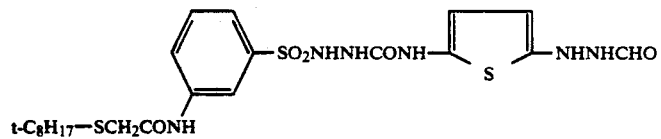
I-90
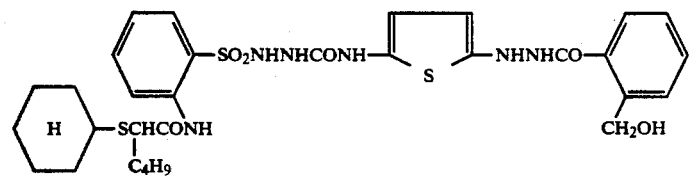
I-91
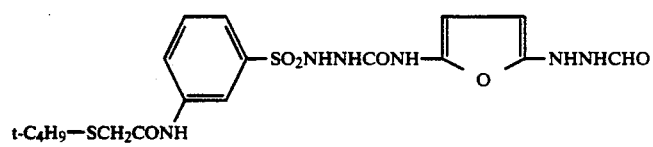
I-92

-continued
Exemplary compounds (I)
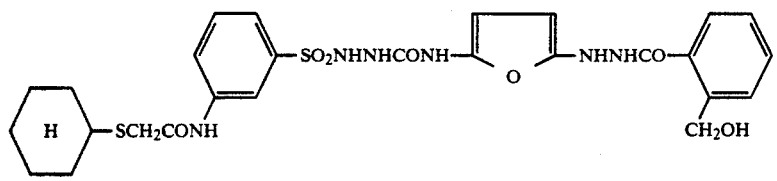
I-93
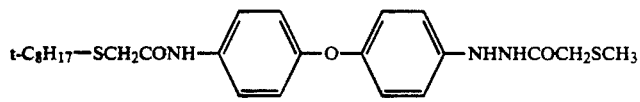
I-94
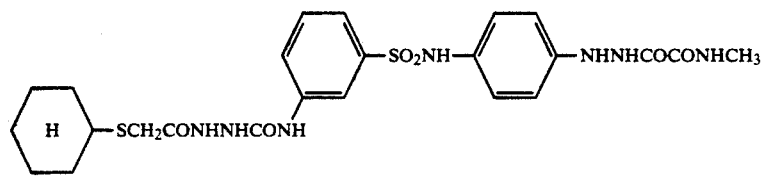
I-95
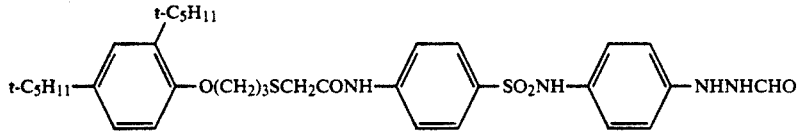
I-96
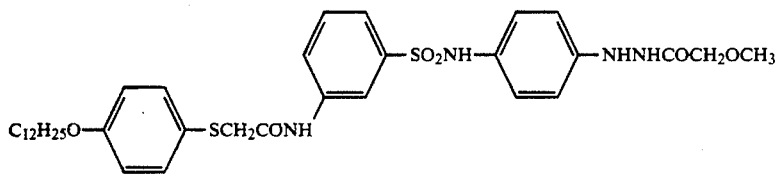
I-97
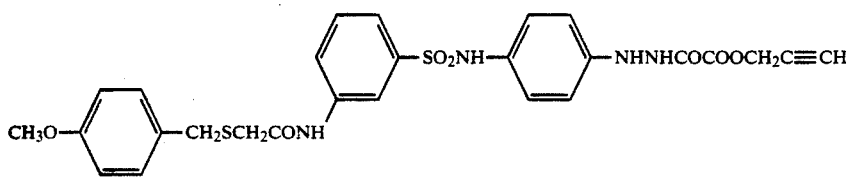
I-98
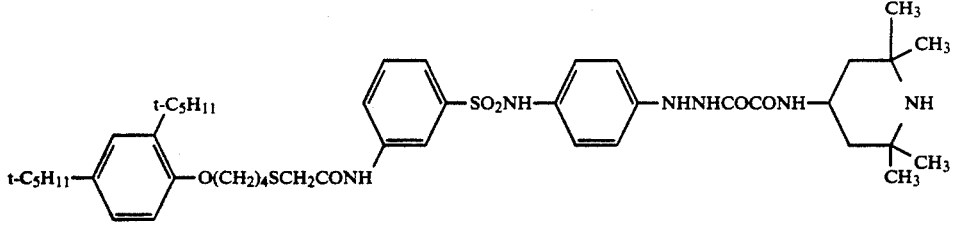
I-99
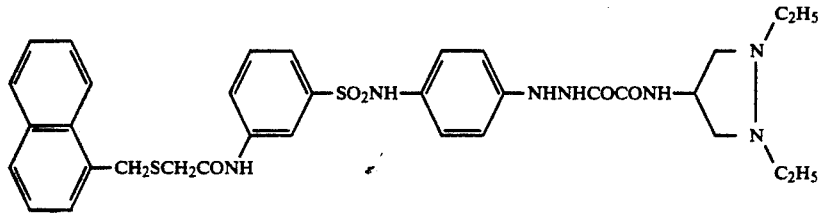
I-100
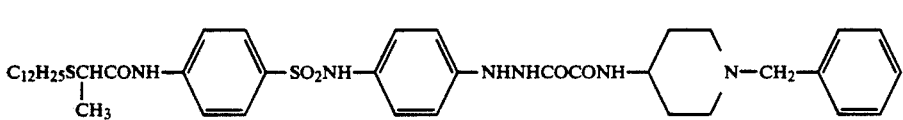
I-101

-continued
Exemplary compounds (I)
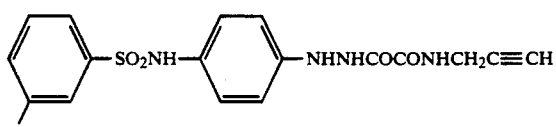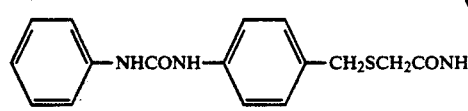 I-102
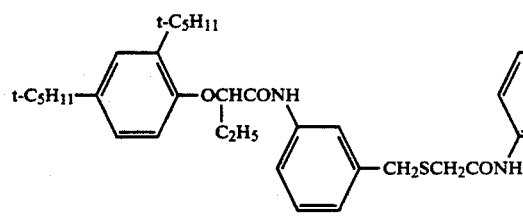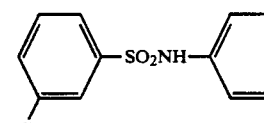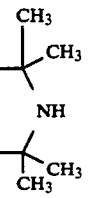 I-103
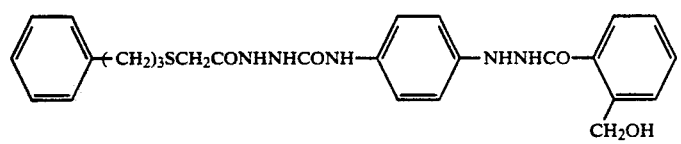 I-104
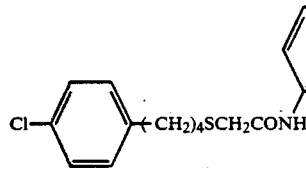 I-105
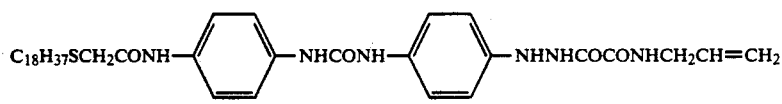 I-106
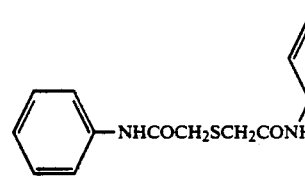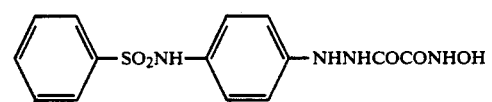 I-107
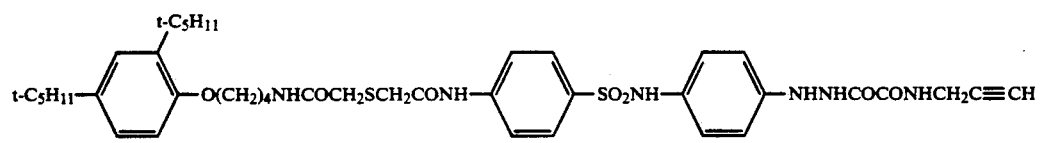 I-108
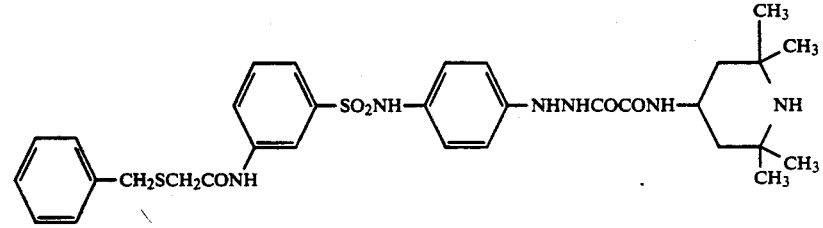 I-109

-continued
Exemplary compounds (I)
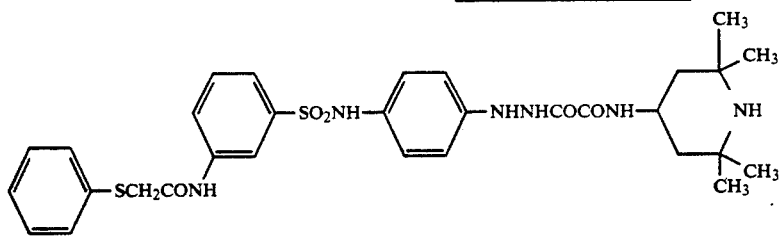
I-110
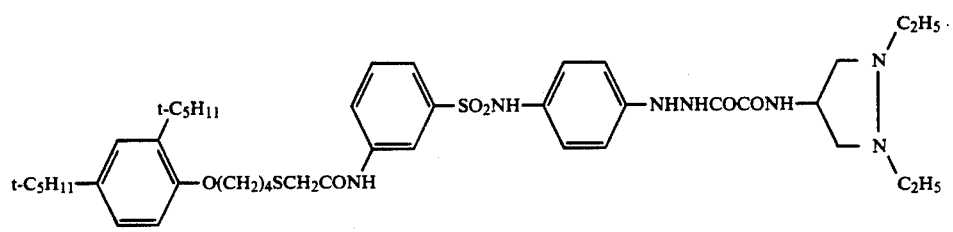
I-111
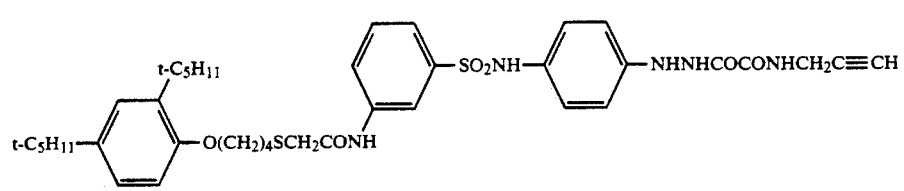
I-112
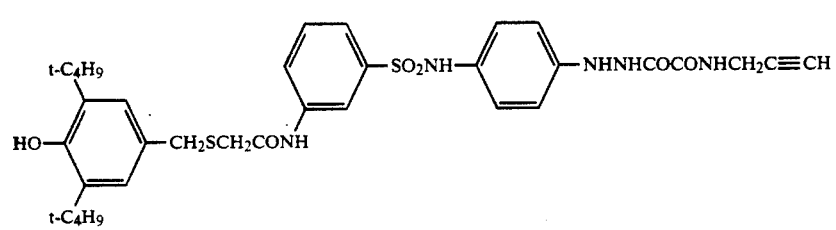
I-113
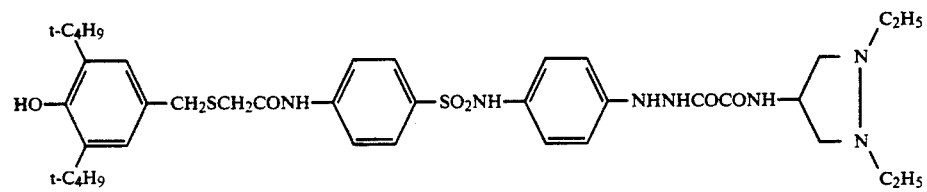
I-114
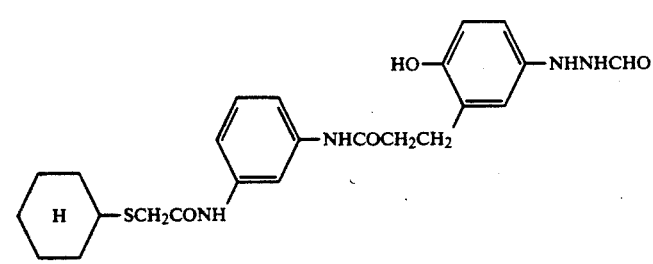
I-115
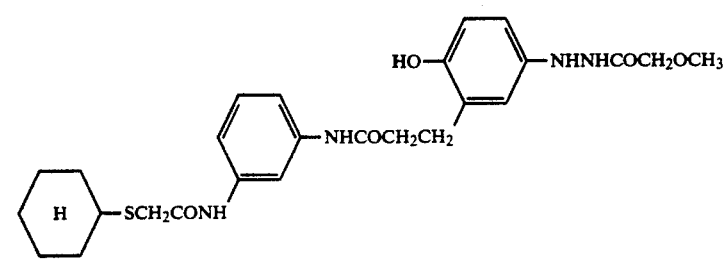
I-116

-continued
Exemplary compounds (I)

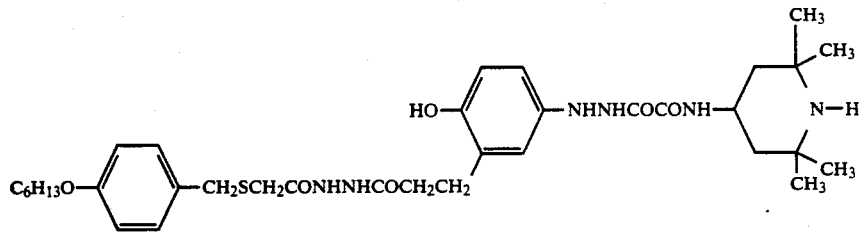
I-117

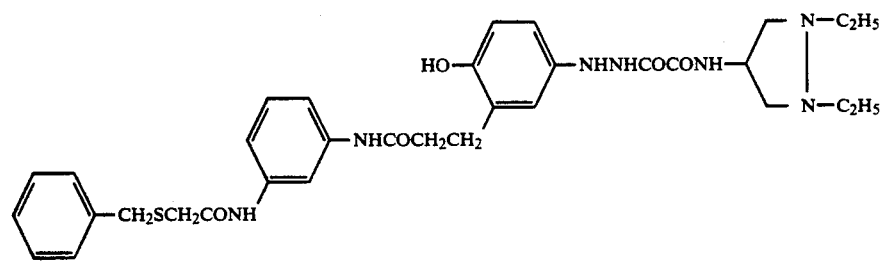
I-118

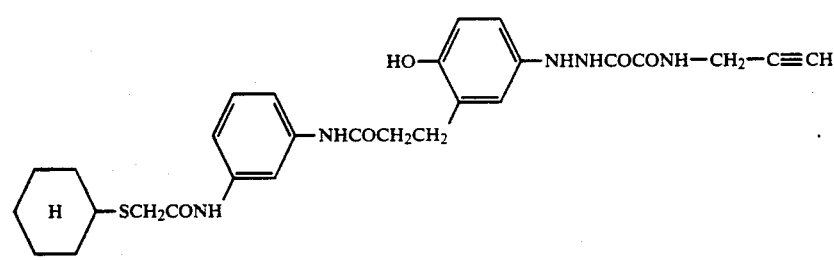
I-119

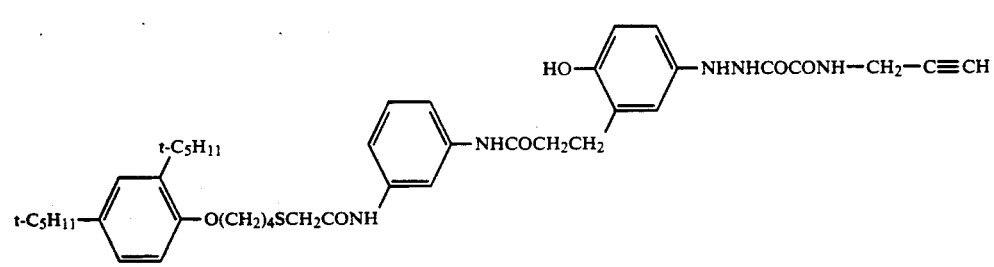
I-120

Synthesis of the compounds to be used in the present invention is described below. To take compound I-1 as an example, it can be synthesized by the following method starting with the intermediate described in JP-A-62-270948:

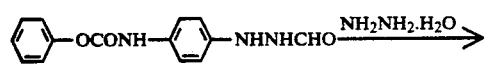

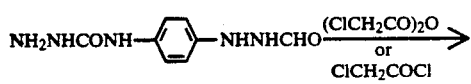

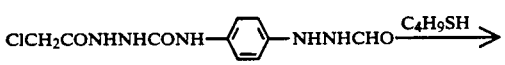

or

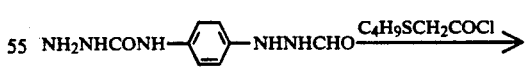

Compound I-3 can be synthesized by the following method starting with the intermediate described in Japanese Patent Application No. 336565/1987:

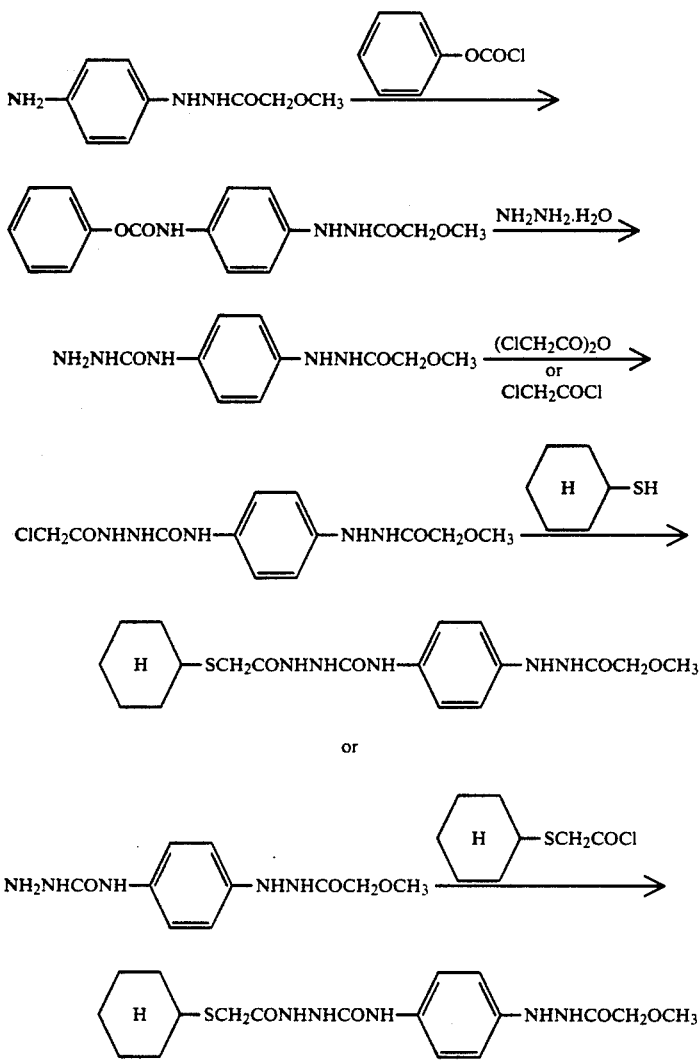
Compound I-36 can be synthesized by the following method:
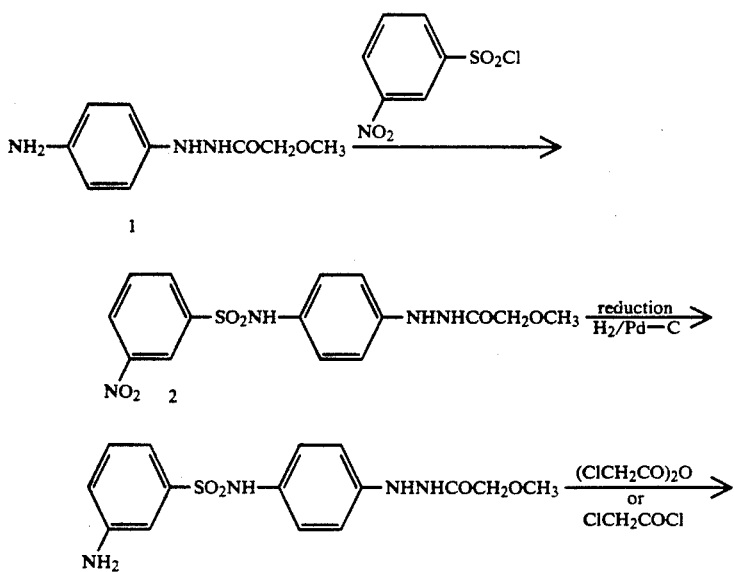

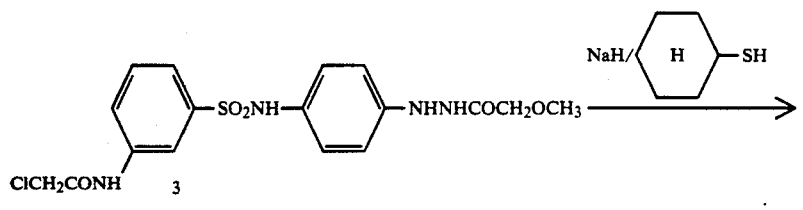
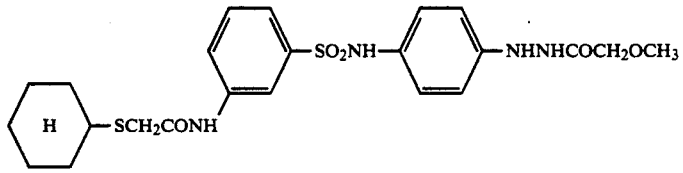
or
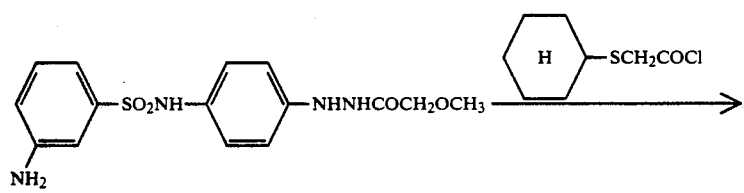
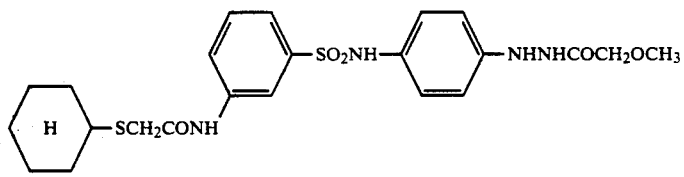
Compound I-44 can be synthesized by the following method starting with the intermediate described in European Patent No. 330,109:
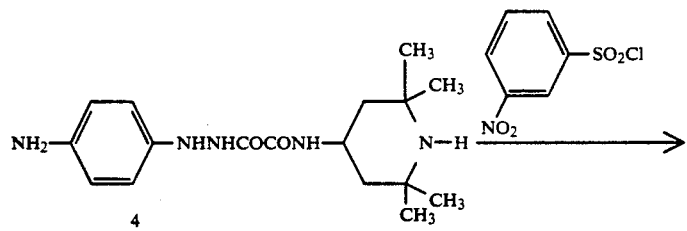
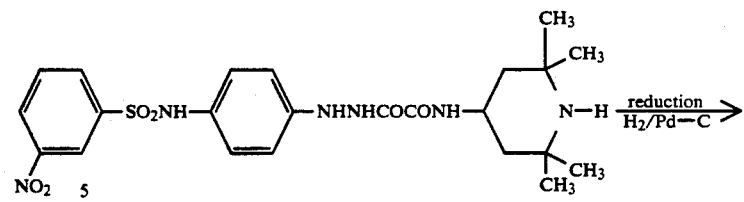
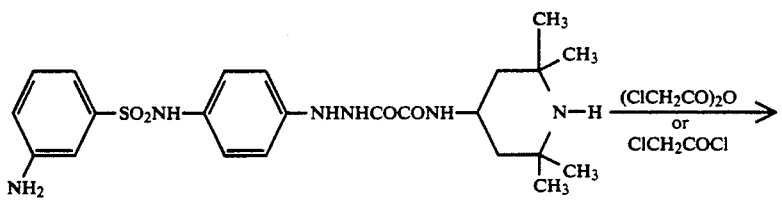

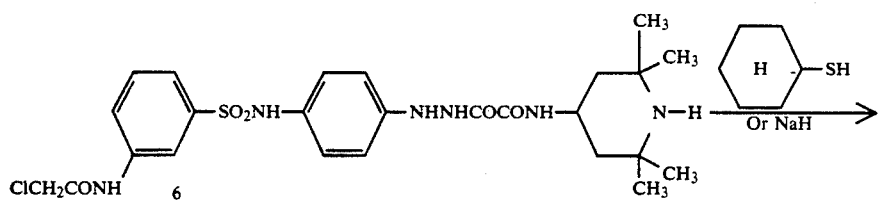
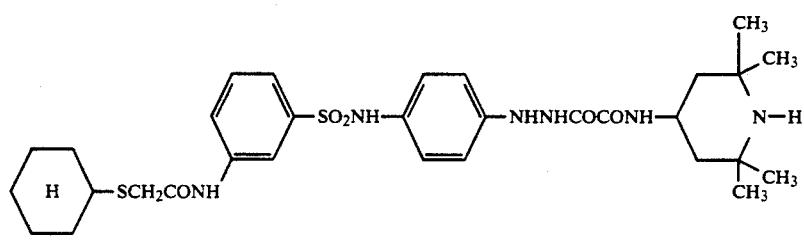
or
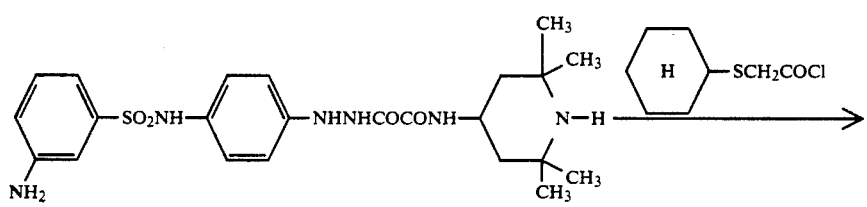
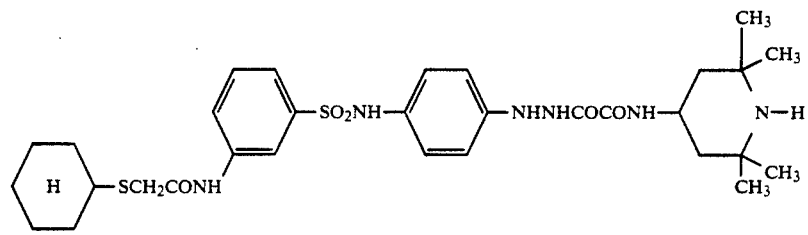
Compound I-72 and I-76 can be synthesized by the following method:
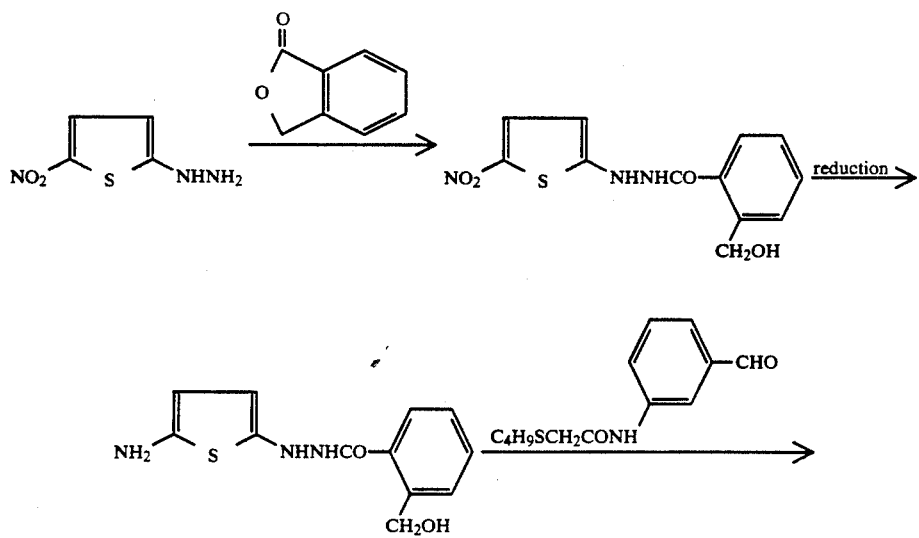

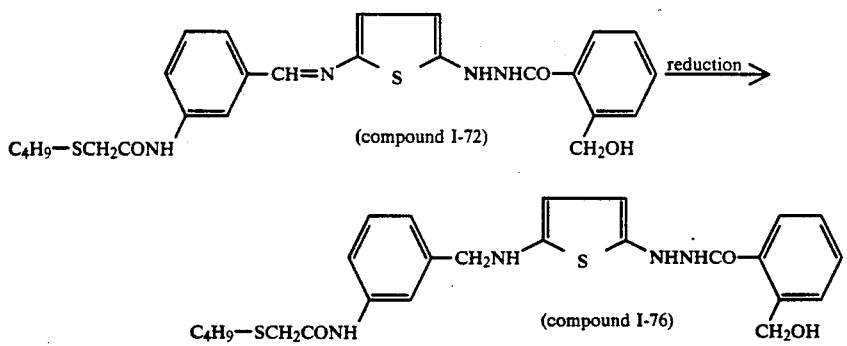

Other compounds of the general formula (I) can be synthesized by similar procedures.

The methods of syntheiszing compounds I-36 and I-44 are described below more specifically.

SYNTHESIS 1 (SYNTHESIS OF COMPOUND I-36)

1-1. Synthesis of compound (2)

A portion (26.0 g or 133 mmol) of compound (1) described in Japanese Patent Application No. 336565/1987 is dissolved in 100 ml of acetic acid. Thereafter, 11.6 g (146 mmol) of pyridine and 32.4 g (146 mmol) of m-nitrobenzene sulfonyl chloride are added and the resulting solution is stirred at room temperature for 1 h. Subsequently, the reaction solution is concentrated and subjected to extraction with ethyl acetate (160 ml) and water (100 ml). The ethyl acetate layer is dried with magnesium sulfate and concentrated to obtain compound (2) in an amount of 43.1 g (yield, 85%).

1-2. Synthesis of compound (3)

A portion (26.0 g or 68 mmol) of compound (2) is suspended in 80 ml of acetic acid. After adding 2 g of 10% Pd/C, reduction with hydrogen is conducted at 40° C. under atmospheric pressure. When hydrogen absoption ends, Pd/C is filtered off and 5.4 g (68 mmol) of pyridine and 7.7 g (68 mmol) of chloroacetyl chloride are added, followed by stirring at room temperature for 2 h. After concentrating the reaction solution, 100 ml of diethyl ether is added for washing and the solution is stirred. After standing, the supernatant is decanted and the residue is dried to obtain an oil of compound (3) in an amount of 29.2 g (yield, 100%).

1-3. Synthesis of I-36

To 50 ml of dry DMF, 8.2 g (204 mmol) of 60% NaH, 2.1 g (14 mmol) of NaI and 8.7 g (75 mmol) of cyclohexanethiol are added. To the resulting mixture, a solution having 29.2 g (68 mmol) of compound (3) dissolved in 100 ml of dry DMF is added dropwise uner cooling with ice. After stirring at room temperature for 2 days, 800 ml of ice water and 400 ml of ethyl acetate are added for extraction. The ethyl acetate layer is concentrated and the resulting oil is purified on a column chromatograph (silica gel eluted with a solvent system of chloroform and methanol), whereby I-36 is obtained in an amount of 6.7 g (yield, 19%). MS (FAB), m/e=507 (M+1).

SYNTHESIS 2 (SYNTHESIS OF COMPOUND I-44)

2-1. Synthesis of compound (5)

A portion (33.3 g or 0.1 mol) of compound (4) described in European Patent No. 330,109 is dissolved in 100 ml of acetic acid. Thereafter, 7.9 g (0.1 mol) of pyridine and 22.2 g (0.1 mol) of m-nitrobenzene sulfonyl chloride are added and the resulting solution is stirred at room temperature for 1 h. Subsequently, the reaction solution is concentrated and stirred for 2 h after adding 670 ml of ethyl acetate and 670 ml of water. The precipitating crystal is recovered by filtration and dried to obtain compound (5) in an amount of 34.5 g (yield, 67%).

2-2. Synthesis of compound (6)

A portion (33.0 g or 63.6 mmol) of compound (5) is suspended in 265 ml of acetic acid. After adding 3 g of 10% Pd/C, reduction with hydrogen is conducted at 40° C. under a pressure of 3 Kg/cm². When hydrogen absorption ends, Pd/C is filtered off and 5.6 g (70 mmol) of pyridine and 7.9 g (70 mmol) of chloroacetyl chloride are added, followed by stirring at room temperature for 1 h. After concentrating the reaction solution, 600 ml of diethyl ether is added and the solution is stirred for 2 h. The precipitating crystal is recovered by filtration and dried to obtain compound (6) in an amount of 35.6 g (yield, 99%).

2-3. Synthesis of I-44

To a solution having 8.1 g (54 mmol) of NaI suspended in 50 ml of dry DMF, a solution having 25.3 g (45 mmol) of compound (6) dissolved in 100 ml of dry DMF is added dropwise at room temperature. Following stirring at room temperature for 2 h, the precipitating NaCl is filtered off. The filtrate is added dropwise, under cooling with ice, to a solution having 2.7 g (90 mmol) of 60% NaH and 5.7 g (50 mmol) of cyclohexanethiol in 50 ml of dry DMF, and the mixture is stirred at room temperature for 35 h. To the stirred mixture, 380 g of ice water is added and extraction is performed with 380 ml of chloroform. Thereafter, the chloroform layer is concentrated and the resulting oil is purified on a column chromatograph (silica gel eluted with a solvent system of chloroform and methanol), whereby I-44 is obtained in an amount of 5.2 g (yield, 18%). m.p. 155°-156° C.; MS (FAB), m/e=645 (M+1).

When the silver halide photographic material of the present invention is used as a light-sensitive material that is capable of exhibiting high-contrast photographic characteristics, the following mode is preferred. A silver halide photographic material that incorporates the concept of the present invention and that is capable of producing a high-contrast image must contain at least one of the compounds of the general formula (I) as a material that works as a contrast increasing agent. The amount of the compound of the general formula (I) that is contained in the photographic material preferably ranges from $5 \times 10^{-7}$ to $5 \times 10^{-1}$ moles per mole of the silver halide contained in said photographic material, with the range of $5 \times 10^{-6}$ to $1 \times 10^{-2}$ being particularly preferred.

The silver halide photographic material must also have at least one silver halide emulsion layer. At least one silver halide emulsion layer may be provided on at least one side of a support or it may be provided on both sides of the support. The silver halide emulsion layer may be coated directly on the support or it may be coated with another layer being interposed such as a hydrophilic colloidal layer that does not contain a silver halide emulsion. If necessary, the silver halide emulsion layer may be overcoated with a hydrophilic colloidal layer as a protective layer. The silver halide emulsion layer may be divided into sub-layers having different degrees of sensitivity, such as a high-sensitivity sub-layer and a low-sensitivity sub-layer. In this case, an intermediate layer such as one composed of a hydrophilic colloid may be provided between sub-layers. If desired, a non-light-sensitive hydrophilic colloidal layer may be provided between the silver halide emulsion layer and the protective layer and examples of such non-light-sensitive hydrophilic colloidal layers include an intermediate layer, a protective layer, an anti-halo layer and a backing layer.

In order to insure that the compound (I) will function properly as a contrast increasing agent, it is preferably incorporated in a hydrophilic colloidal layer in the photographic material. It is particularly preferred that said compound is incorporated in a silver halide emulsion layer and/or in an adjacent hydrophilic colloidal layer.

The silver halide to be used in the silver halide photographic material of the present invention is described below.

Any silver halide composition may be used, as exemplified by silver chloride, silver chlorobromide, silver chloroiodobromide, pure silver bromide, silver iodobromide, or silver chloroiodobromide. Silver halide grains preferably have an average grain size of 0.05–0.5 μm, with the range of 0.10–0.40 μm being particularly preferred.

The silver halide grains to be used in the present invention may have any size distribution but those having a value of 1–30 for monodispersity as defined below are preferred. More preferably, the value of monodispersity is adjusted to lie within the range of 5–20.

The term "monodispersity" as used hereinabove is defined by the following formula:

$$\text{Monodispersity} = \sqrt{\frac{\Sigma (\bar{r} - ri)^2 ni}{\Sigma ni}} \div \bar{r} \times 100$$

In other words, monodispersity is defined as the standard deviation of a grain size that is divided by the average grain size and multiplied by 100. The size of a silver halide grain is conveniently expressed by the length of one side if it is a cubic grain and by the square root of the projected area if it is in other crystal forms (e.g. octahedra and tetradecahedra).

In the practice of the present invention, silver halide grains having a two or more layered structure may be used. For instance, core/shell type silver chlorobromide or chloroiodobromide grains may be used, with the core being made of silver chloride or silver iodobromide and the shell being made of silver bromide, or conversely the core being made of silver bromide and the shell being made of silver chloride. In this case, iodine may be incorporated in any layer in an amount not exceeding 5 mol %.

In the process of forming and/or growing silver halide grains to be used in a silver halide emulsion, metal ions may be added using at least one metal salt selected from among a cadmium salt, a zinc salt, a lead salt, a thallium salt, an iridium salt (or a complex salt thereof), a rhodium salt (or a complex salt thereof) and an iron salt (or a complex salt thereof), whereby these metals in elemental form are incorporated in the interior and/or surface of the grains. If desired, the grains may be placed in a suitable reducing atmosphere in order to impart reduction sensitization nuclei to the interior and/or surface of the grains.

Silver halides may be sensitized with various chemical sensitizers. Exemplary chemical sensitizers include: activated gelatin; sulfur sensitizers (e.g. sodium thiosulfate, allyl thiocarbamide, thiourea and ally lisocyanate); selenium sensitizers (e.g. N,N-dimethylselenourea and selenourea); reduction sensitizers (e.g. triethylenetetramine and stannous chloride); and noble metal sensitizers (e.g. potassium chloroaurite, potassium aurithiocyanate, potassium chloroaurate, 2-aurosulfobenzothiazole methyl chloride, ammonium chloropalladate, potassium chloroplatinate, and sodium chloropalladite). These chemical sensitizers may be used either on their own or as admixtures When gold sensitizers are to be used, ammonium thiocyanate may be used as an aid.

When the concept of the present invention is to be applied to light-sensitive materials that are capable of producing a high-contrast image, the silver halide grains may preferably be applied as those having a higher sensitivity in the surface than in the interior in order to provide negative image. Hence, their performance can be enhanced by treatment with the chemical sensitizers described above.

The silver halide emulsion to be used in the present invention may be stabilized or rendered resistant against fogging by treatment with mercapto compounds (e.g. 1-phenyl-5-tetrazole and 2-mercaprobenzothiazole), benzotriazoles (e.g. 5-bromobenzotriazole and 5-methylbenzotriazole), and benzimidazoles (e.g. 6-nitrobenzimidazole). Addenda such as spectral sensitizers, plasticizers, antistats, surfactants, hardeners and development accelerators may also be added to the silver halide emulsion for use in the present invention.

When the compound represented by the general formula (I) is to be added to a hydrophilic colloidal layer, gelatin is preferably used as a binder in said collidal layer but other hydrophilic colloids than gelatin may also be used.

Examples of the support that can be used in the practice of the present invention with photographic materials intended to produce high-contrast image include baryta paper, polyethylene-coated paper, synthetic polypropylene paper, glass sheet, cellulose acetate film, cellulose nitrate film, and films of polyesters such as polyethylene terephthalate. A suitable support may be selected depending upon a specific use of silver halide photographic materials.

The following developing agents may be used to develop silver halide photographic materials for producing high-contrast image: HO—(CH=CH)$_n$—OH type developing agents, representative examples of which are hydroquinone, catechol and pyrogallol; HO—(CH=CH)$_n$—NH$_2$ type developing agents, representative examples of which are ortho- and para-aminophenols and aminopyrazolones such as N-methyl-p-aminophenol, N-β-hydroxyethyl-p-aminophenol, p-hydroxyphenylaminoacetic acid and 2-aminophenol; heterocyclic developing agents exemplified by 3-pyrazolidones such as 1-phenyl-3-pyrazolidone, 1-phenyl-4,4-dimethyl-3-pyrazolidone, 1-phenyl-4-methyl-4-hydroxymethyl-3-pyrazolidone and 1-phenyl-4-methyl-4-hydroxymethyl-3-pyrazolidone.

Other developing agents that can be used be used effectively in the present invention are described in T. H. James, "The Theory of the Photographic Process", Forth Edition, pp. 291-334, Macmillan Publishing Co., Inc., 1977, and Journal of the American Chemical Society, Vol. 73, p. 3,100,1951.

The developing agents described above may be used either on their own or as admixtures. Preferably, they are used as admixtures. When only one developing agent is to be used, hydroquinone is preferred. If two developing agents are to be used in combination, hydroquinone is preferably combined with either 1-phenyl-3-pyrazolidone or N-methyl-p-aminophenol.

The developing solutions to be used in developing photographic materials in accordance with the present invention may contain sulfites (e.g. sodium sulfite and potassium sulfite) as preservatives without compromising the advantages of the present invention. Hydroxylamine or hydrazide compounds may also be used as preservatives. In order to achieve pH adjustment and buffering action, caustic alkalis, alkali carbonates or amines may be used as in the case of common black-and-white developing solutions. Various other additives may also be incorporated and they include: inorganic development restrainers such as potassium bromide; organic development restrainers such as benzotriazole; metal ion sequestering agents such as ethylenediaminetetraacetic acid; development accelerators such as methanol, ethanol, benzyl alcohol and polyalkylene oxides; surfactants such as sodium alkylarysulfonates, natural saponin, saccharides and alkyl esters of these compounds; hardeners such as glutaraldehyde, formaldehyde and glyoxal; and ionic strength adjusting agents such as sodium sulfate.

Developing solutions for use in the present invention may also contain organic solvents such as alkanolamines and glycols.

The photographic material of the present invention may also be used as a direct positive light-sensitive material and in this case the following mode is preferred.

In the case under consideration, the compound represented by the general formula (I) can be used as a foggant. In the following description, the compound (I) which functions as a foggant shall be named "the foggant of the present invention".

At least one of the foggants of the present invention may be incorporated in such a way that it fogs an internal latent image forming silver halide emulsion (i.e. an emulsion that provides a direct positive image) during development after imagewise exposure. Stated more specifically, the foggant of the present invention only need be incorporated in the light-sensitive material in such a way that said light-sensitive material which contains an internal latent image forming silver halide emulsion can be developed in the presence of said foggant after exposure.

In a particularly preferred embodiment, at least one of the foggants of the present invention is incorporated in a silver halide emulsion layer or an adjacent layer thereto (e.g. a silver halide light-sensitive layer, an intermediate layer, a filter layer, a protective layer or an anti-halo layer).

The amount in which the foggant of the present invention is used can vary over a broad range depending on the characteristics of the silver halide emulsion used, the type of foggant and the conditions of development but it only need be used in an amount that provides a positive image when the photographic material having an internal latent image forming silver halide emulsion is developed with a surface developing solution after imagewise exposure. Desirably, the amount of the foggant to be used is such that it is sufficient to provide an adequate maximum density (e.g. 2.0 or more) after development.

The foggant of the present invention is preferably incorporated in the silver halide emulsion in such a way that at a suitable time after the end of ripening, the foggant is present in an amount of ca. $10^{-5}$ to $10^{-1}$ mole per mole of silver halide.

Silver halide developing agents that can be used in the step of development in the practice of the present invention include hydroquinones, catechols, aminophenols, 3-pyrazolidones, ascorbic acid or derivatives thereof, reductones, phenylenediamines and mixtures thereof. If desired, these developing agents may be preliminarily incorporated in the emulsion so that they will act on silver halides during immersion in high-pH aqueous solutions.

The developing composition to be used in developing the direct positive silver halide photographic material in the practice of the present invention may further contain specified antifoggants and development restrainers. If desired, such developing composition may be incorporated in any coating or layer in the silver halide photographic material. Useful antifoggants include: benzotriazoles such as 5-methylbenzotriazole; benzothiazoles such as 5-methylbenzothiazole; heterocyclic thiones such as 4-methyl-2-tetrazoline-5-thione; and aromatic or aliphatic mercapto compounds such as 1-phenyl-5-mercaptotetrazole.

When the concept of the present invention is applied to a direct positive silver halide photographic material, the silver halide emulsion to be used is an internal latent image forming silver halide emulsion, namely an emulsion that has silver halide grains in the interior of which a latent image is to be predominantly formed and which contain in its interior the greater part of sensitivity specks. Any silver halides may constitute such emulsions and they include, for example, silver bromide, silver chloride, silver chlorobromide, silver iodobromide and silver chloroiodobromide.

A suitable emulsion may be determined by conducting the following test: part of a sample having an emulsion of interest coated on a transparent support is exposed to a light intensity scale for a fixed period up to about one second and subsequently developed at 20° C. for 4 min with a surface developing solution A having the recipe shown below which is substantially free from a silver halide solvent and which develops only the surface image on the grains; another part of the same emulsion sample is exposed similarly and developed at 20° C. for 4 min with an internal developing solution B having the recipe shown below which develops the internal image in the grains. A preferred emulsion is such that the maximum density achieved by development with solution A is not higher than a fifth of the maximum density achieved by development with solution B. More preferably, the maximum density achieved by development with solution A is not higher than a tenth of the maximum density achieved by development with solution

| Surface developing solution A | |
| --- | --- |
| Metol | 2.5 g |
| L-Ascorbic acid | 10 g |
| NaBO$_2$.4H$_2$O | 20 g |
| KBr | 1 g |
| Water | to make 1,000 ml |
| Internal developing solution B | |
| Metol | 2.0 g |
| Sodium sulfite (anhydrous) | 90.0 g |
| Hydroquinone | 8.0 g |
| Sodium carbonate (H$_2$O) | 52.5 g |
| KBr | 5.0 g |
| KI | 0.5 g |
| Water | to make 1,000 ml |

The internal latent image forming silver halide emulsions to be used in the present invention may be prepared by various methods and exemplary emulsions include: the "converted" silver halide emulsion described in U.S. Pat. No. 2,592,250; the silver halide emulsion containing internally chemically sensitized silver halide grains as described in U.S. Pat. Nos. 3,206,316, 3,317,322, 3,367,778 and JP-B-43-29405; the silver halide emulsion having silver halide grains incorporating polyvalent metal ions as described in U.S. Pat. Nos. 3,271,157, 3,447,927 and 3,531,291; the silver halide emulsion comprising grains having a multilayered structure as described in JP-A-50-8524; and the silver halide emulsion containing silver iodide grains prepared by the ammoniacal method as described in Japanese Patent Application No. 74062/1976.

Compounds having an azaindene ring or nitrogenous heterocyclic compounds having a mercapto group may be contained in the internal latent image forming silver halide emulsions in preferred amounts of 1 mg–10 g per mole of silver halide and this is effective for the purpose of achieving more consistent results at a lower minimum density. A preferred example of the compounds having an azaindene ring is 4-hydroxy-6-methyl-1,3,3a,7-tetrazaindene. Exemplary nitrogenous heterocyclic compounds having a mercapto group include a pyrazole ring, 1,2,4-triazole ring, 1,2,3-triazole ring, 1,3,4-thiadiazole ring, 1,2,3-thiadiazole ring, 1,2,4-thiadiazole ring, 1,2,5-thiadiazole ring, 1,2,3,4-tetrazole ring, pyridazine ring, 1,2,3-triazine ring, 1,2,4-triazine ring, 1,3,5-triazine ring, and rings consisting of two or three of these rings condensed together as exemplified by a triazolotriazole ring, diazaindene ring, triazaindene ring, tetrazaindene ring, pentazaindene ring, as well as phthalazinone and indazole rings. Among these, 1-phenyl-5-mercaptotetrazole is preferred.

The silver halide photographic material of the present invention, if it is to be used as a positive light-sensitive material, may be a black-and-white photographic material or a monochromatic or multi-color photographic material. If it is to be used as a full-color photographic material, it is preferably designed to have a blue-sensitive a green-sensitive and a red-sensitive layer. In this case, the photographic material is usually formed of a blue-sensitive silver halide emulsion layer containing a yellow coupler, a green-sensitive silver halide emulsion layer containing a magenta coupler, and a red-sensitive silver halide emulsion layer containing a cyan coupler.

In a preferred embodiment, the blue-sensitive, green-sensitive and red-sensitive layers are superposed on a support in such a way that the blue-sensitive layer being the remotest from the support, with a non-light-sensitive layer (yellow filter layer) being provided between the blue sensitive and green-sensitive layers.

Known acylacetanilide compounds may be used as yellow couplers and among them benzoylacetanilide and pivaloylacetanilide compounds are used with particular advantage. Usable as magenta couplers include 5-pyrazolone compounds, pyrazoloazole compounds and open-chain acylacetonitrile compounds. Naphtholic and phenolic compounds may preferably be used as cyan couplers.

Besides the light-sensitive silver halide emulsion layers and the non-light-sensitive layer which serves as a yellow filter layer, the support may also have provided thereon many other photographic constituent layers such as an intermediate layer, a protective layer, a subbing layer, a backing layer and an anti-halo layer. These layers may be coated by any suitable method such as dip coating, air-doctor coating, extrusion coating, sliding hopper coating or curtain flow coating.

When the silver halide photographic material of the present invention is to be used as a direct positive light-sensitive material, various supports may be used, as exemplified by polyethylene terephthalate films, polycarbonate films, polystyrene films, polypropylene films, cellulose acetate films, glass sheets, baryta paper and polyethylene laminated paper. These supports may be subbed as required. These supports may be opaque or transparent depending on the type of light-sensitive material to be used.

The silver halide emulsion in the light-sensitive material may contain various photographic additives such as a wetting agent, a film property improving agent and a coating aid in accordance with the specific object of use. Other photographic additives that can be used include a gelatin plasticizer, a surfactant, a uv absorber, a pH modifier, an antioxidant, an antistat, a thickener, a granularity improving agent, a dye, a mordant, a brightening agent, a development speed modifier and a matting agent.

In order to prevent the fading of dye image due to actinic radiation at shorter wavelengths, uv absorbers such as thiazolidone, benzotriazole, acrilonitrile and benzophenone compounds can advantageously be used.

Gelatin and appropriate gelatin derivatives (which should be selected depending on the object) may be used as a protective colloid or binder in the silver halide emulsion layer. Depending on the object, other hydrophilic binders may also be used. Such binders may be added to the emulsion layer or other photographic constituent layers such as an intermediate layer, a protective layer, a filter layer and a backing layer. A plasticizer or wetting agent as appropriate for a specific object may be incorporated in the hydrophilic binders.

The individual photographic conssituent layers of the light-sensitive material may be hardened with any suitable hardeners.

The light-sensitive material may also have as AS (antistain) agent incorporated therein.

The following examples are provided for the purpose of further illustrating the present invention but are in no way to be taken as limiting.

EXAMPLE 1

Compounds of the general formula (I) and comparative compounds (for their type, see Table 1 to be given later in this specification) were added to silver halide emulsion layers, thereby preparing samples of photographic material.

Preparation of silver halide photographic material

A polyethylene terephthalate film 100 μm was coated with a subbing layer 0.1 μm on both sides. A silver halide emulsion layer to the following recipe (1) was coated on one subbing layer to give a gelatin deposit of 1.5 g/m² and a silver deposit of 3.3 g/m². A protective layer to the following recipie (2) was coated on the emulsion layer to give a gelatin deposit of 1.0 g/m². A backing layer to the following recipe (3) was coated on the other subbing layer to give a gelatin deposit of 3.5 g/m². A protective layer to the following recipe (4) was further coated on the baking layer to give a gelatin deposit of 1 g/m². In this way, sample Nos. 1-13 were prepared.

Recipe (1) of silver halide emulsion layer

| | |
|---|---|
| Gelatin | 1.5 g/m² |
| Chlorobromide silver emulsion (60 mol % AgCl and 40 mol % AgBr; monodispersity = 12) | 3.3 g/m² |
| Antifoggant: 4-hyroxy-6-methyl-1,3,3a,7-tetrazaindene | 0.30 g/m² |
| Compound of the invention or comparative compound | See Table 1 |
| Surfactant: saponin | 0.1 g/m² |
| Latex polymer: polyethyl acrylate | 1 g/m² |

Spectral sensitizer: The following four compounds of structural formulas (A)-(D) were used blue sensitizer

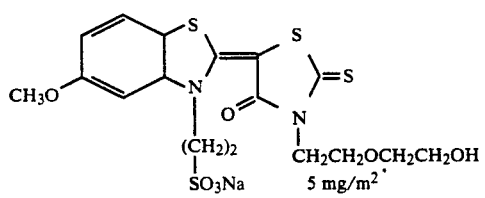

(A)

5 mg/m² green sensitizer (B)-1

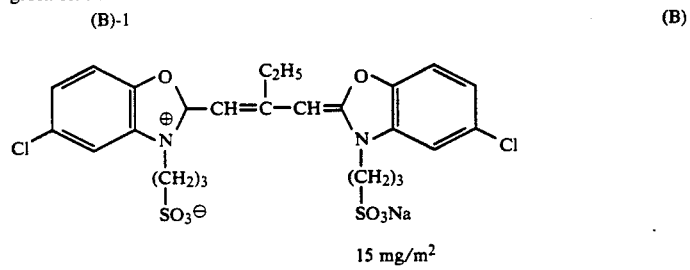

(B)

15 mg/m²

(B)-2

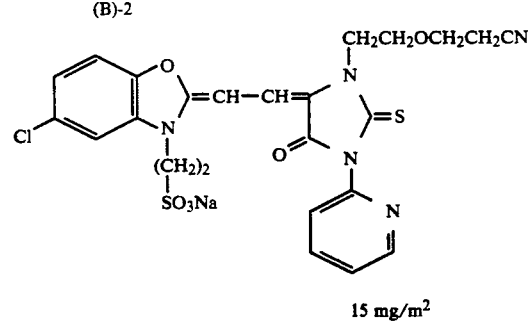

15 mg/m² red sensitizer

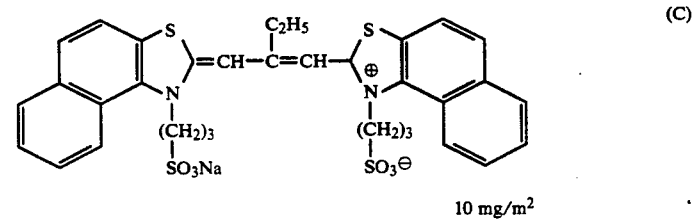

(C)

10 mg/m² infrared sensitizer

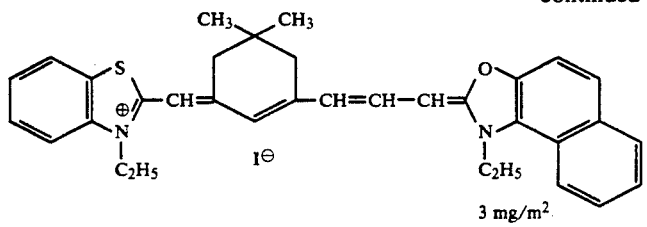

3 mg/m² (D)

Development control agent:

| | |
|---|---|
| Nonylphenoxypolyethylene glycol | 10 mg/m² |
| 5-Methylbenzotriazole | 7 mg/m² |
| Adenine | 3 mg/m² |
| Guanine | 2 mg/m² |
| Uracil | 2 mg/m² |
| 1-Phenyl-5-mercaptotetrazole | 3 mg/m² |
| Hydroquinone | 100 mg/m² |
| 1-Phenyl-3-pyrazolidone | 10 mg/m² |

Recipe (2) of emulsion protective layer

| | |
|---|---|
| Gelatin | 1.0 g/m² |
| Matting agent: polymethyl methacrylate with average particle size of 3.0–5.0 μm | 0.05 g/m² |
| Surfactant: Sodium n-dodecyl-benzenesulfonate | 0.01 g/m² |
| Charge modifier: | |
| C₈F₁₇COONH₄ | 10 mg/m² |
| NaCl | 100 mg/m² |
| LiCl | 30 mg/m² |
| Formulation stabilizer: | |
| [benzimidazole-SH structure, NaO₃S substituent] | 5 mg/m² |
| 1-phenyl-5-mercaptotetrazole | 3 mg/m² |
| Hardener: formaldehyde | 0.03 g/m² |

Recipe (3) of backing layer

| | |
|---|---|
| Gelatin | 3.5 g/m² |
| Dye: | |

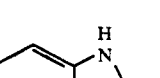

1 g/m²

[triphenylmethane dye structure] 1 g/m²

| | |
|---|---|
| Surfactant: saponin | 0.1 g/m² |
| Hardener: glyoxal | 0.1 g/m² |

Recipe (4) of backing protective layer

| | |
|---|---|
| Gelatin | 1 g/m² |
| Matting agent: polymethyl methacrylate with average particle size of 3.0–5.0 μm | 0.5 g/m² |
| Surfactant: sodium p-dodecylbenzene sulfonate | 0.01 g/m² |
| $C_8F_{17}SO_2NH(CH_2)_3\overset{+}{N}(CH_3)_2-CH_2COO^-$ | 0.01 g/m² |
| Development control agent: | |
| 5-nitroindazole | 0.012 g/m² |
| 5-methylbenzotriazole | 0.02 g/m² |
| 1-phenyl-5-mercaptotetrazole | 0.005 g/m² |
| Hardener: formaldehyde | 0.03 g/m² |

The samples thus prepared were subjected to a dot quality test by the following procedure.

Method of dot quality test

A step wedge was attached to a crossline screen (dot area, 50%; 150 lines/inch) and the sample placed in intimate contact with the screen was exposed to light from a xenon lamp for 5 seconds. The exposed sample was processed under the conditions specified below with a rapid automatic processor charged with a developing solution and a fixing solution that had the recipes also shown below. The dots in the halftone image on the processed sample were examined with a magnifier (×100) and the dot quality was evaluated by the following criteria: 5, excellent; 4, good; 3, fair; 2, mediocre; 1, poor.

The fog in the dots was examined in a similar way and the results were evaluated by the following criteria: 5, no "pepper fog" in dots; 4, 3, 2 and 1 in the decreasing quality in terms of the occurrence of "pepper fog".

Recipe of the developing solution

| | |
|---|---|
| Composition A: | |
| Pure water (ion-exchanged water) | 150 ml |
| Ethylenediaminetetraacetic acid | 2 g |

-continued

| | |
|---|---|
| disodium salt | |
| Diethylene glycol | 50 g |
| Potassium sulfite (55% w/v aq. sol.) | 100 ml |
| Potassium carbonate | 50 g |
| Hydroquinone | 15 g |
| 5-Methylbenzotriazole | 200 mg |
| 1-Phenyl-5-mercaptotetrazole | 30 mg |
| Potassium hydroxide | q.s. to attain pH 10.4 |
| Potassium bromide | 3 g |
| Composition B: | |
| Pure water (ion-exchaned water) | 8 ml |
| Diethylene glycol | 50 g |
| Diethylamino-1,2-propanediol | 15 g |
| Ethylenediaminetetraacetic acid disodium salt | 25 mg |
| Acetic acid (90% aq. sol.) | 0.3 ml |
| 5-Nitroindazole | 110 mg |
| Sodium 2-mercaptobenzimidazole-5-sulfonate | 30 mg |
| 1-Phenyl-3-pyrazolidone | 500 mg |

Just prior to use, compositions A and B were dissolved, in the order written, into 500 ml of water and worked up to 1,000 ml.

Recipe of the fixing solution

| | |
|---|---|
| Composition A: | |
| Ammonium thiosulfate (72.5% w/v aq. sol.) | 240 ml |
| Sodium sulfite | 17 g |
| Sodium acetate (3H$_2$O) | 6.5 g |
| Boric acid | 6 g |
| Sodium citrate (2H$_2$O) | 2 g |
| Acetic acid (90% w/w aq. sol.) | 13.6 ml |
| Composition B: | |
| Pure water (ion-exchanged water) | 17 ml |
| Sulfuric acid (50% w/w aq. sol.) | 4.7 g |
| Aluminum sulfate (aq. sol. with 8.1% w/w of Al$_2$O$_3$) | 26.5 g |

Just prior to use, compositions A and B were dissolved, in the order written, into 500 ml of water and worked up to 1,000 ml. The pH of the resulting fixing solution had a pH of ca. 4.3.

Processing scheme

| Step | Temperature, °C | Time, sec |
|---|---|---|
| Development | 38 | 30 |
| Fixing | 28 | 20 |
| Washing | R.T. | 20 |

The following compounds (a)-(c) were used as comparative compounds to be incorporated in the silver halide emulsion to recipe (1):

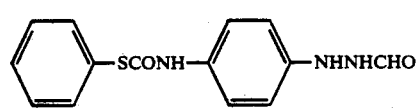

(a)

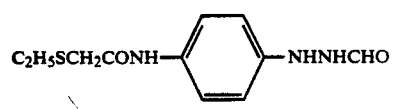

(b)

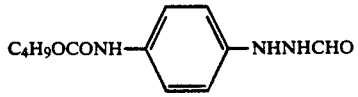

(c)

Test results

Table 1 identifies the compounds incorporated in the silver halide emulsion layer in sample Nos. 1-10 of the present invention and comparative sample Nos. 11-13, together with the amounts in which those compounds were used. The compounds of the general formula (I) shown in Table 1 are identified by the numbers with which they are labelled hereinabove in the list of "Exemplary Compounds (I)".

Table 2 shows the results of dot quality and pepper fog evaluations on a five-score rating basis.

As is clear from Table 2, sample Nos. 1-10 of the present invention ranked "4" in terms of dot quality but comparative sample Nos. 11-13 ranking "3" were inferior. It is therefore apparent that sample Nos. 1-10 of the present invention are very satisfactory in terms of dot quality.

As for "pepper fog", sample Nos. 1-10 of the present invention ranked either "5" or "4", indicating their excellent quality in terms of fog. In contrast, comparative sample Nos. 11-13 ranked "2" and hence were not satisfactory in terms of fog.

The same test was conducted with compounds I-96, I-99, I-111 and I-112 of the present invention and all samples tested ranked at least "4" in terms of both dot quality and pepper fog.

TABLE 1

| Sample No. | Compound | Amount (per mol Ag) | Remarks |
|---|---|---|---|
| 1 | 1 | 5 × 10$^{-4}$ mol | |
| 2 | 2 | 5 × 10$^{-4}$ mol | |
| 3 | 3 | 5 × 10$^{-4}$ mol | |
| 4 | 4 | 5 × 10$^{-4}$ mol | |
| 5 | 28 | 5 × 10$^{-4}$ mol | Invention |
| 6 | 30 | 5 × 10$^{-4}$ mol | |
| 7 | 32 | 5 × 10$^{-4}$ mol | |
| 8 | 36 | 5 × 10$^{-4}$ mol | |
| 9 | 44 | 5 × 10$^{-4}$ mol | |
| 10 | 63 | 5 × 10$^{-4}$ mol | |
| 11 | a | 5 × 10$^{-4}$ mol | |
| 12 | b | 5 × 10$^{-4}$ mol | Comparison |
| 13 | c | 5 × 10$^{-4}$ mol | |

TABLE 2

| Sample No. | Dot quality | Pepper fog | Remarks |
|---|---|---|---|
| 1 | 5 | 4 | |
| 2 | 5 | 4 | |
| 3 | 4 | 5 | |
| 4 | 5 | 5 | |
| 5 | 4 | 4 | Invention |
| 6 | 5 | 5 | |
| 7 | 4 | 5 | |
| 8 | 5 | 4 | |
| 9 | 5 | 4 | |
| 10 | 5 | 5 | |
| 11 | 3 | 2 | |
| 12 | 3 | 2 | Comparison |
| 13 | 3 | 2 | |

EXAMPLE 2

Additional sample Nos. 14-23 were prepared as in Example 1 except that the monodispersity (for its definition, see above) of silver halide grains in sample Nos. 3 and 9 was changed to values between 4 and 40.

During the preparation of silver halide grains, rhodium and iridium were incorporated in the usual manner in respective amounts of $8 \times 10^{-7}$ mol and $3 \times 10^{-7}$ mol per mole of Ag. The silver halide grains thus prepared were AgClBr grains with 98 mol % AgCl. In place of spectral sensitizers (A)-(D), a desensitizing dye having the following structure was added:

Desensitizing dye (having a positive sum of the anode and cathode potentials on polarograph):

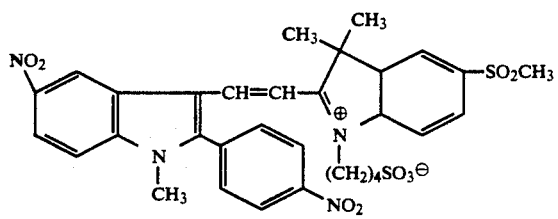

The following filter dye was also added (50 mg/m²) to the protective layer:

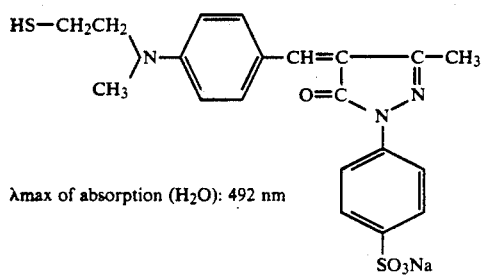

λmax of absorption (H₂O): 492 nm

The following uv absorber was further added (100 mg/m²):

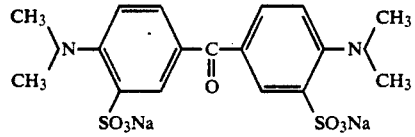

The other features of sample Nos. 14-23 were the same as sample Nos. 3 and 9; for example, they used compound I-3 or I-44 as a compound of the general formula (I). The monodispersity of silver halide grains could be adjusted by a conventional controlled double-jet method with the pH potential and the supply of Ag+ and halide ions being varied during the charging of starting solutions.

Exposure and development procedures were also substantially the same as in Example 1 and the photographic performance of the samples was evacuated. The only exception was that exposure was performed under an ultrahigh-pressure mercury lamp at an energy of 5 mJ.

The results of evaluation are shown in Table 3, from which one can see that sample Nos. 14-23 ranked 4.5-5 in terms of both dot quality and pepper fog. Hence, those samples of the present invention had very high dot quality and experienced very small fog.

TABLE 3

| Sample No. | Compound | Monodispersity of silver halide grains | Photographic performance | |
|---|---|---|---|---|
| | | | Dot quality | Pepper fog |
| 14 | 3 | 40 | 4.5 | 4.5 |
| 15 | 3 | 35 | 4.7 | 4.6 |
| 16 | 3 | 20 | 4.8 | 4.7 |
| 17 | 3 | 10 | 5 | 5 |
| 18 | 3 | 4 | 5 | 5 |
| 19 | 44 | 40 | 4.5 | 4.5 |
| 20 | 44 | 35 | 4.7 | 4.8 |
| 21 | 44 | 20 | 4.8 | 4.8 |
| 22 | 44 | 10 | 5 | 5 |
| 23 | 44 | 4 | 5 | 5 |

EXAMPLE 3

The procedure of Example 1 was repeated except in the following points: the silver halide emulsion was changed to the formula set forth below; only green sensitizer (B)-1 was used as a spectral sensitizer; (CH₂=CHSO₂CH₂)₂O was used as the hardener in recipe (2) in an amount of 0.10 g/m²; the developing solution was prepared according to the recipe shown below; and the compounds of the present invention and the comparative compounds were selected and used in the amounts shown in Table 4.

Preparation of silver halide emulsion

A silver iodobromide emulsion (2 mol % AgI per mole Ag) was prepared by a double-jet method, during which K₂IrCl₆ was added in an amount of $6 \times 10^{-7}$ moles per mole of Ag. The resulting emulsion comprised cubic grains with an average size of 0.20 μm. It was washed with water and desalted in the usual manner and had pAg (40° C.) adjusted to 8.80 using an aqueous solution of potassium iodide. Further, during the redispersing step, a mixture of the following compounds (A), (B) and (C) was added.

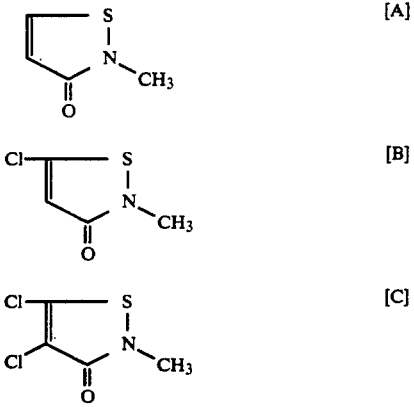

Recipe of the developing solution

| | |
|---|---|
| Hydroquinone | 45.0 g |
| N-Methyl-p-aminophenol hemisulfate | 0.8 g |
| Sodium hydroxide | 18.0 g |
| Potassium hydroxide | 55.9 g |
| 5-Sulfosalicylic acid | 45.0 g |
| Boric acid | 25.0 g |
| Potassium sulfite | 110.0 g |
| Ethylenediaminetetraacetic acid disodium salt | 1.0 g |
| Potassium bromide | 6.0 g |
| 5-Methylbenzotriazole | 0.6 g |

| | -continued | |
|---|---|---|
| n-Butyldiethanolamine | | 15.0 g |
| Water to make | | 1.000 ml |
| | | (pH = 11.0) |

The processed samples were subjected to a dot quality test in the same manner as in Example 1. Further, they were measured for density with a Konica digital densitometer PDP-65. The results are shown in Table 4 in terms of relative sensitivity, with the value for sample No. 29 at a density of 3.0 being taken as 100. Gamma values are also shown in Table 4 ($\gamma$=the tangent of the angle the straight line connecting densities of 0.3 and 3.0 forms with the horizontal axis of the characteristic curve).

As is clear from Table 4, the samples of the present invention were more sensitive and contrasty than the comparative samples. The also showed better dot quality and experienced less "pepper fog".

TABLE 4

| Sample No. | Compound Type | Amount (per mol Ag) | Relative sensitivity | Gamma | Dot quality | Pepper fog | Remarks |
|---|---|---|---|---|---|---|---|
| 24 | 12 | $1 \times 10^{-3}$ mol | 109 | 10.9 | 5 | 5 | Invention |
| 25 | 40 | $1 \times 10^{-3}$ mol | 112 | 11.0 | 5 | 4 | |
| 26 | 48 | $1 \times 10^{-3}$ mol | 111 | 11.2 | 5 | 5 | |
| 27 | 58 | $1 \times 10^{-3}$ mol | 109 | 10.8 | 4 | 5 | |
| 28 | 75 | $1 \times 10^{-3}$ mol | 112 | 11.1 | 5 | 4 | |
| 29 | a | $1 \times 10^{-3}$ mol | 100 | 9.8 | 3 | 2 | Comparison |
| 30 | b | $1 \times 10^{-3}$ mol | 105 | 10.5 | 3 | 2 | |
| 31 | c | $1 \times 10^{-3}$ mol | 100 | 9.8 | 3 | 2 | |

In another experiment, sample Nos. 24–28 were processed under the same conditions as described above except that the pH of the developing solution was changed to 10.8. Sample Nos. 24–28 of the present invention ranked at least 4 in terms of both dot quality and pepper fog. Also, they had gamma values of at least 10.

EXAMPLE 4

Preparation of emulsion A

A monodispersed silver bromide emulsion was prepared in the manner described below.

To a vigorously stirred aqueous solution of ossein gelatin held at 70° C., an aqueous solution of silver nitrate and an aqueous solution of potassium bromide were added simultaneously by a controlled double-jet method. An octahedral emulsion having an average grain size of 0.4 μm was obtained. The emulsion was chemically ripened by heating at 75° C. for 80 min in the presence of 5 mg of sodium thiosulfate and 6 mg of chloroauric acid (4H$_2$O) per mole of silver, whereby a silver bromide core emulsion was obtained. The core emulsion was grown by adding an aqueous solution of silver nitrate and an aqueous solution of potassium bromide and sodium chloride (50:50 in molar ratio) until an octahedral monodispersed core/shell silver chlorobromide emulsion having an average grain size of 0.7 μm was obtained. After washing with water and desalting, sodium thiosulfate and chloroauric acid (4H$_2$O) were added in a respective amount of 1.3 mg per mole of silver and the mixture was then heated at 60° C. for 70 min to perform chemical sensitization, whereby an internal latent image forming silver halide emulsion was obtained.

Preparation of samples

Sample No. 32 was prepared by coating seven layers (for their composition, see below) on a paper support laminated with polyethylene on both sides.

Sample No. 32 (Unless otherwise noted, the amounts of all compounds used are expressed as "deposit weight" in mg/dm; the amounts of emulsions are expressed in terms of silver; for the structures of specific compounds, see below)

| Seventh layer (protective layer): | |
|---|---|
| Gelatin | 12.3 |
| Sixth layer (uv absorbing layer): | |
| Gelatin | 5.4 |
| UV absorber (UV-1) | 1.0 |
| UV absorber (UV-2) | 2.8 |
| Solvent (SO-3) | 1.2 |
| Fifth layer (blue-sensitive layer): | |
| Emulsion A (containing spectral sensitizer BD-1) | 5.0 |
| Gelatin | 13.5 |
| Yellow coupler (YC-1) | 8.4 |
| Image stabilizer (AO-3) | 3.0 |
| Solvent (SO-1) | 5.2 |
| Compound (a) | $5 \times 10^{-3}$ mol/mol Ag |
| Fourth layer (yellow filter layer): | |
| Gelatin | 4.2 |
| Yellow colloidal silver | 1.0 |
| UV absorber (UV-1) | 0.5 |
| UV absorber (UV-2) | 1.4 |
| Antistain agent (AS-1) | 0.4 |
| Solvent (SO-8) | 0.8 |
| Third layer (green-sensitive layer): | |
| Emulsion A (containing spectral sensitizer GD-1) | 2.7 |
| Gelatin | 13.0 |
| Magenta coupler (MC-1) | 2.4 |
| Image stabilizer (AO-1) | 2.0 |
| Solvent (SO-4) | 3.15 |
| Compound (a) | $5 \times 10^{-8}$ mol/mol Ag |
| Second layer (antistain layer): | |
| Gelatin | 7.5 |
| Antistain agent (AS-1) | 0.55 |
| Solvent (SO-2) | 0.72 |
| First layer (red-sensitive layer): | |
| Emulsion A (containing spectral sensitizers RD-1 and RD-2) | 4.0 |
| Gelatin | 13.8 |
| Cyan coupler (CC-1) | 2.1 |
| Cyan coupler (CC-2) | 2.1 |
| Image stabilizer (AO-3) | 2.2 |
| Solvent (SO-1) | 3.3 |
| Compound (a) | $5 \times 10^{-8}$ mol/mol Ag |

When coating operations were performed, SA-1 and SA-2 were used as coating aids, and HA-2 as a hardener.

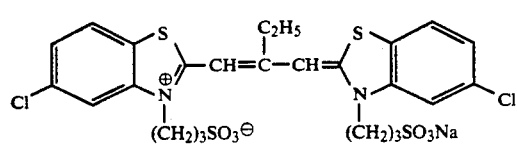 RD-1
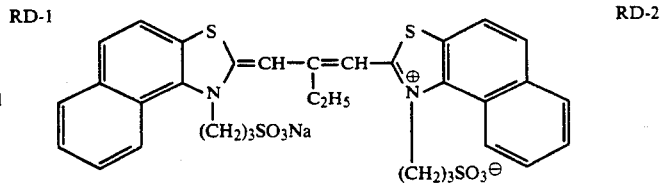 RD-2
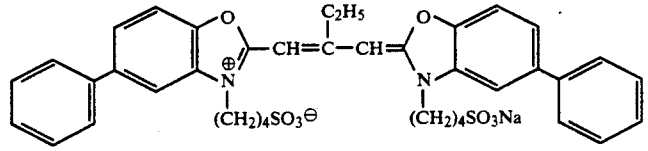 GD-1
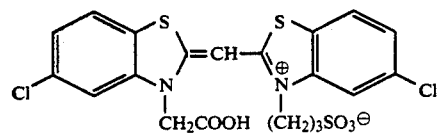 BD-1
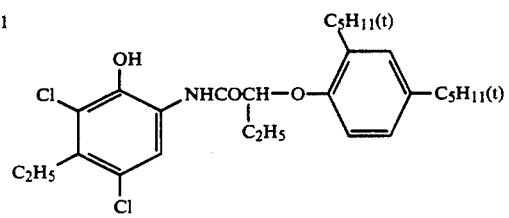 CC-1
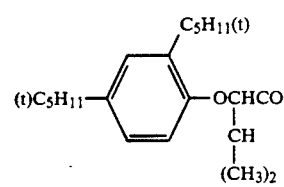 CC-2
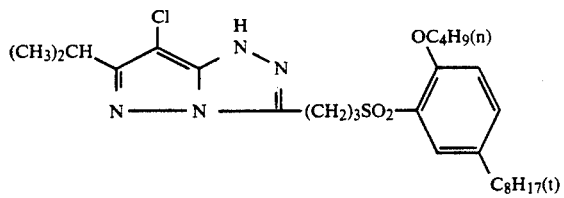 MC-1
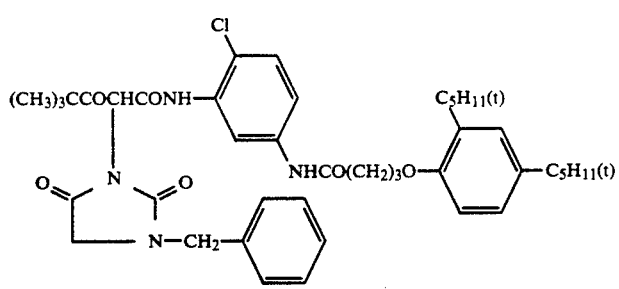 YC-1
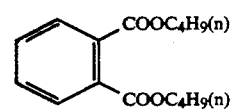 SO-1
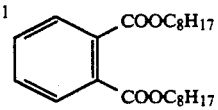 SO-2
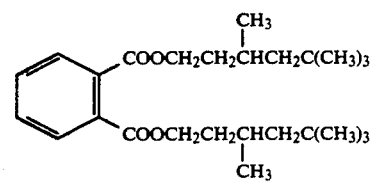 SO-3
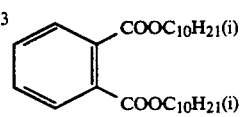 SO-4

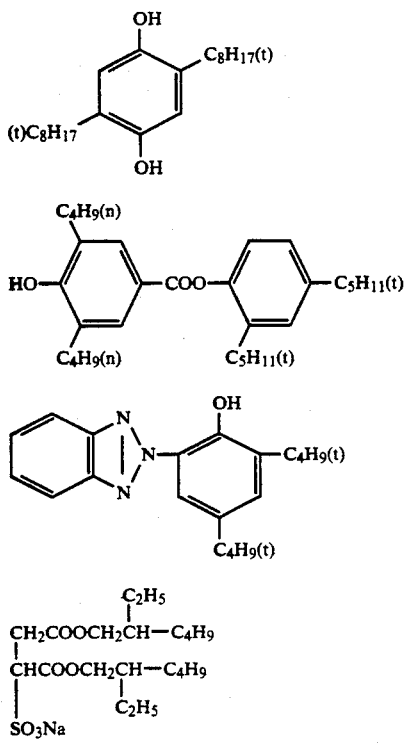

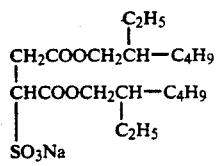

-continued

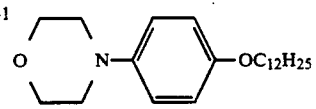
AS-1

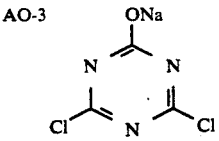
AO-3

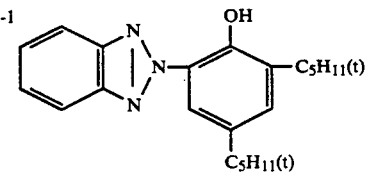
UV-1

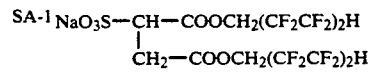
SA-1 NaO$_3$S—CH—COOCH$_2$(CF$_2$CF$_2$)$_2$H
         |
         CH$_2$—COOCH$_2$(CF$_2$CF$_2$)$_2$H AO-1: morpholine-N-phenyl-OC$_{12}$H$_{25}$

HA-2

UV-2

SA-2

Additional sample Nos. 33–39 were prepared in entirely the same manner as sample No. 32 except that compound (a) in each light-sensitive layer was changed to compound (b), (c) or the foggants of the present invention represented by the general formula (I) (for their specific type, see Table 5).

Compounds (a), (b) and (c) used as comparative foggants were the same as comparative compounds (a), (b) and (c) used in Example 1.

The prepared samples were exposed through an optical wedge using a sensitometer and subsequently processed in accordance with the following schemes.

| Scheme 1 | | |
|---|---|---|
| Step | Time | Temperature, °C. |
| Color development | 2 min | 33 |
| Bleach-fixing | 40 sec | 33 |
| Stabilizing | 20 sec × 3 | 33 |
| Drying | 30 sec | 60–80 |

| Recipe of color developing solution | |
|---|---|
| Diethylenetriaminepentaacetic acid | 2.0 g |
| Benzyl alcohol | 12.8 g |
| Diethylene glycol | 3.4 g |
| Sodium sulfite | 2.0 g |
| Sodium bromide | 0.5 g |
| Hydroxylamine sulfate | 2.6 g |
| Sodium chloride | 3.2 g |
| 3-Methyl-4-amino-N-ethyl-N-($\beta$-methane-sulfonamidoethyl)aniline | 4.25 g |
| Potassium carbonate | 30.0 g |
| Optical brightening agent (4,4'-diamino-stilbenedisulfonic acid derivative) | 1.0 g |
| Water to make | 1,000 ml |
| pH | adjusted 10.5 with potassium hydroxide and sulfuric acid |

| Recipe of bleach-fixing solution | |
|---|---|

-continued

| | |
|---|---|
| Ammonium thiosulfate (54 wt %) | 150 cc |
| Sodium sulfite | 15 g |
| Ethylenediaminetetraacetic acid iron (III) ammonium salt | 55 g |
| Ethylenediaminetetraacetic acid sodium salt (2H$_2$O) | 4 g |
| Glacial acetic acid | 8.61 g |
| Water to make | 1,000 ml |
| pH | adjusted to 5.4 with aqueous ammonia or HCl |

| Recipe of stabilizing solution | |
|---|---|
| 1-Hydroxyethylidene-1,1'-diphosphonic acid (60%) | 1.6 ml |
| Bismuth chloride | 0.35 g |
| Polyvinylpyrrolidone | 0.25 g |
| Aqueous ammonia | 2.5 ml |
| Nitrilotriacetic acid (3Na) | 1.0 g |
| 5-Chloro-2-methyl-4-isothiazolin-3-one | 50 mg |
| 2-Octyl-4-isothiazolin-3-one | 50 mg |
| Optical brightening agent (4,4'-diamino-stilbene compound) | 1.0 g |
| Water to make | 1,000 ml |
| pH | adjusted to 7.5 with potassium hydroxide or HCl |

Scheme 2

Same as scheme 1 except that the pH of the color developing solution was adjusted to 11.0.

The processed samples were subjected to sensitometry and the maximum density (Dmax) and minimum density (Dmin) of the magenta image on each sample were measured. The results are shown in Table 5 below.

TABLE 5

| Sample No. | Compound | Magenta image | Scheme 1 | Scheme 2 | Remarks |
|---|---|---|---|---|---|
| 32 | a | Dmax | 1.68 | 1.88 | Comparison |

TABLE 5-continued

| Sample No. | Compound | Magenta image | Scheme 1 | Scheme 2 | Remarks |
|---|---|---|---|---|---|
|  |  | Dmin | 0.18 | 0.19 |  |
| 33 | b | Dmax | 1.79 | 1.98 |  |
|  |  | Dmin | 0.16 | 0.17 |  |
| 34 | c | Dmax | 1.70 | 1.91 |  |
|  |  | Dmin | 0.18 | 0.19 |  |
| 35 | 33 | Dmax | 2.02 | 2.15 | Invention |
|  |  | Dmin | 0.12 | 0.14 |  |
| 36 | 41 | Dmax | 2.04 | 2.19 |  |
|  |  | Dmin | 0.13 | 0.16 |  |
| 37 | 45 | Dmax | 2.00 | 2.12 |  |
|  |  | Dmin | 0.12 | 0.14 |  |
| 38 | 51 | Dmax | 2.03 | 2.18 |  |
|  |  | Dmin | 0.13 | 0.16 |  |
| 39 | 71 | Dmax | 2.02 | 2.22 |  |
|  |  | Dmin | 0.13 | 0.15 |  |

As is clear from Table 5, sample Nos. 35–39 containing the antifoggants of the present invention provided satisfactory positive images that had a higher maximum density but lower minimum density than comparative sample Nos. 32–34 even when they were processed at low pH.

EXAMPLE 5

Additional sample Nos. 40–47 were prepared as in Example 4 except that the foggants were changed to the compounds shown in Table 6. One group of these samples were immediately exposed as in Example 4 and processed in accordance with scheme 1. The minimum density (Dmin) of the magenta image on each sample was measured.

Another group of the raw samples (yet to be exposed and developed) were subjected to aging by keeping them at 50° C. and 80% r.h. for 3 days. Thereafter, the samples were exposed and processed in accordance with scheme 1 and the minimum density, (Dmin)', of the magenta image on each sample was also measured. The values of Dmin and (Dmin)' are shown in Table 6, from which one can see that compared to sample Nos. 40–42 containing known foggants, sample Nos. 43–47 containing the foggants of the present invention experienced a smaller increase in minimum density of magenta image even when they were processed after storage. It is therefore clear that the samples of the present invention has good raw stock stability.

TABLE 6

| Sample No. | Compound | Dmin | (Dmin)' | Remarks |
|---|---|---|---|---|
| 40 | a | 0.18 | 0.30 | Comparison |
| 41 | b | 0.16 | 0.28 |  |
| 42 | c | 0.18 | 0.27 |  |
| 43 | 53 | 0.11 | 0.16 | Invention |
| 44 | 62 | 0.11 | 0.15 |  |
| 45 | 84 | 0.13 | 0.17 |  |
| 46 | 85 | 0.11 | 0.15 |  |
| 47 | 87 | 0.12 | 0.17 |  |

The present invention provides a silver halide photographic material that is contrasty, that has good dot quality, that experiences limited fog and that yet has high sensitivity. If this photographic material is used as a direct positive light-sensitive-material, a satisfactorily high maximum density can be obtained even if it is processed with a developing solution having low pH. Further, a satisfactory positive image having high maximum density and low minimum density can be produced by performing fogging development for a comparatively short time. As a further advantage, the increase in minimum density is very small even if the photographic material is stored for a while prior to exposure and subsequent processing.

What is claimed is:

1. A silver halide photographic material comprising a silver halide emulsion layer, wherein said silver halide photographic material contains a compound represented by the following general formula (I):

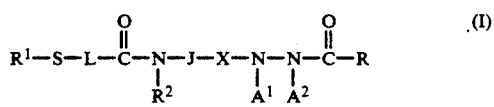

where $R^1$ is an unsubstituted alkyl or an alkyl substituted by at least one group selected from the group consisting of aryl, hetero cyclic ring, hydroxy, unsubstituted alkoxy, sulfonamido, aryloxy, ureido, carbamoyl, acylamino and sulfamoyl, $R^2$ is a hydrogen atom, an alkyl group, an aryl group or a heterocyclic ring, R is a hydrogen atom or a blocking group; L is an alkylene or alkenylene group; J is a linkage group; X is an aromatic or heterocyclic residue; $A^1$ and $A^2$ are each a hydrogen atom, or either one of them is a hydrogen atom and the other is an acyl, sulfonyl or oxalyl group.

2. The silver halide photographic material according to claim 1 which is a printing light-sensitive material containing the compound of the general formula (I) as a contrast increasing agent.

3. The silver halide photographic material according to claim 2 wherein the compound of the general formula (I) is incorporated in an amount of $5 \times 10^{-7}$ to $5 \times 10^{-1}$ moles per mole of silver halide.

4. The silver halide photographic material according to claim 2 wherein the compound of the general formula (I) is contained in the emulsion layer and/or an adjacent layer thereto.

5. The silver halide photographic material according to claim 1 which is a direct positive light-sensitive material containing the compound of the general formula (I) as a foggant.

6. The silver halide photographic material according to claim 5 wherein the compound of the general formula (I) is contained in the emulsion layer and/or an adjacent layer thereto.

7. The silver halide photographic material according to claim 5 wherein the compound of the general formula (I) is incorporated in an amount of $10^{-5}$ to $10^{-1}$ mole per mole of silver halide.

* * * * *